United States Patent
Mio et al.

(10) Patent No.: US 7,015,236 B2
(45) Date of Patent: Mar. 21, 2006

(54) N-HETEROARYLNICOTINAMIDE DERIVATIVES

(75) Inventors: Shigeru Mio, Shiga (JP); Hideshi Okui, Shiga (JP)

(73) Assignee: Sankyo Agro Company, Limited, Tokyo (JP)

( * ) Notice: Subject to any disclaimer, the term of this patent is extended or adjusted under 35 U.S.C. 154(b) by 0 days.

(21) Appl. No.: 10/495,897

(22) PCT Filed: Nov. 19, 2002

(86) PCT No.: PCT/JP02/12078

§ 371 (c)(1),
(2), (4) Date: May 17, 2004

(87) PCT Pub. No.: WO03/044013

PCT Pub. Date: May 30, 2003

(65) Prior Publication Data

US 2005/0004368 A1   Jan. 6, 2005

(30) Foreign Application Priority Data

Nov. 21, 2001 (JP) ............................. 2001-355561
Mar. 11, 2002 (JP) ............................. 2002-065193

(51) Int. Cl.
  *A01N 43/74*  (2006.01)
  *C07D 413/12*  (2006.01)

(52) U.S. Cl. ..................................... 514/340; 546/272.1

(58) Field of Classification Search ............. 546/272.1; 514/340

See application file for complete search history.

(56) References Cited

FOREIGN PATENT DOCUMENTS

| | | |
|---|---|---|
| EP | 744400 A2 | 11/1996 |
| JP | 7-10841 A | 1/1995 |
| JP | 7-25853 A | 1/1995 |
| JP | 9-3046 A | 1/1997 |
| JP | 9-328471 A | 12/1997 |
| WO | WO 00/35913 A1 | 6/2000 |
| WO | WO 00/58288 A1 | 10/2000 |
| WO | WO 02/48111 A2 | 6/2002 |

OTHER PUBLICATIONS

Yamamoto et al., "1,3-Oxazines and Related Compounds, etc.," Heterocycles, 9 (2) (1978), pp. 185-192.*

* cited by examiner

*Primary Examiner*—Patricia L. Morris
(74) *Attorney, Agent, or Firm*—Frishauf, Holtz, Goodman & Chick, P.C.

(57) ABSTRACT

An N-heteroaryl-4-(haloalkyl)nicotinamide derivative represented by formula (I):

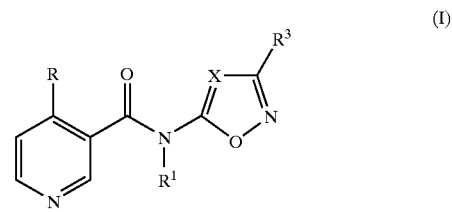

[wherein R represents a $C_1$–$C_6$ haloalkyl group; $R^1$ represents a hydrogen atom, a $C_1$–$C_6$ alkyl group which may be substituted a $C_2$–$C_6$ alkenyl group or an acyl group; X represents a group represented by formula C—$R^2$, or a nitrogen atom; $R^2$ and $R^3$ each independently represent a hydrogen atom, a halogen atom, a $C_1$–$C_6$ alkyl group which may be substituted, a $C_3$–$C_7$ cycloalkyl group, a $C_2$–$C_6$ alkenyl group, a $C_3$–$C_7$ cycloalkenyl group, a formyl group, a group represented by formula CH=$NOR^4$, a cyano group, a phenyl group which may be substituted, a heterocyclic group which may be substituted, a $C_1$–$C_6$ alkoxy group which may be substituted, a $C_1$–$C_6$ alkylthio group or a phenoxy group]; or a salt thereof, a pesticide containing it as an active component, a method for producing it and intermediates thereof.

20 Claims, No Drawings

N-HETEROARYLNICOTINAMIDE DERIVATIVES

This application is the United States national phase application of International Application PCT/JP02/12078 filed Nov. 19, 2002.

FIELD OF THE INVENTION

The present invention relates to specific N-heteroaryl-4-(haloalkyl)nicotinamide derivatives, salts thereof and pesticides containing them as an active component.

Further, the present invention relates to a method for producing the N-heteroaryl-4-(haloalkyl)nicotinamide derivatives and intermediates thereof.

BACKGROUND ART

In recent years, some of commercially available insecticides are restricted in their use in view of problems of persistency, accumulation and environmental pollution. Further, by using the same type of insecticides for a long period of time, generation of resistant pest insects is growing to be a problem. Therefore, it has been desired to develop an insecticide having a novel structure, which is considered to have a mode of action different from that of the commercially available insecticides.

Heretofore, as the N-heteroaryl-4-(trifluoromethyl)nicotinamide derivative, for example, Japanese Provisional Patent Publication No. Hei 10-195072 describes compounds having a 2-thiazolyl group or a 1,3,4-thiadiazole group as a heteroaryl group, and noxious animal controllers containing those as an active component. However, these compounds are different in the heteroaryl group from those of the invention in this application, and moreover, are insufficient in an insecticidal effect thereof.

Furthermore, a 4-trifluoromethylpyridine having a cyano group, a carbamoyl group or a carboxyl group at position 3 is useful as a manufacturing material of pesticides or medicines, and can be a intermediate of the N-heteroaryl-4-(trifluoromethyl)nicotinamide derivative.

As a production method of this intermediate, conventionally known are Journal of Medicinal Chemistry, vol. 10, 1967, pp. 149–154, Japanese Provisional Patent Publication No. Hei 6-321903, Japanese Provisional Patent Publication No. Hei 7-10841 and Japanese Provisional Patent Publication No. 2000-38385, etc. Among these, Journal of Medicinal Chemistry, vol. 10, 1967, pp. 149–154 describes that 3-cyano-4-trifluoromethylpyridine is an intermediate for the production of a lipolysis inhibitor produced by converting a cyano group into a tetrazolyl group. Further, Japanese Provisional Patent Publication No. Hei 6-321903, Japanese Provisional Patent Publication No. Hei 7-10841 and Japanese Provisional Patent Publication No. 2000-38385 describe that 4-trifluoromethylpyridine having a cyano group or a carbamoyl group at position 3 is an intermediate for the production of a noxious animal controller.

However, the above-described methods have a problem that the number of steps is large or a step having rigorous reaction conditions is contained; therefore, it has been desired to develop a more industrially advantageous production method.

DISCLOSURE OF THE INVENTION

As a result of extensive investigations on a 4-(haloalkyl)nicotinamide derivative, the present inventors have found that a specific N-heteroaryl-4-(haloalkyl)nicotinamide derivative has extremely excellent insecticidal activities against various kinds of harmful insects, and the present invention has been accomplished.

Furthermore, the present inventors have found a novel method for producing the N-heteroaryl-4-(haloalkyl)nicotinamide derivative. In particular, the present inventors have found an industrially advantageous method for inexpensively and simply producing in a high yield a 4-substituted pyridine compound having a cyano group, a carbamoyl group or a carboxyl group at position 3, which is the production intermediate. The present invention has been accomplished based on this finding.

The present invention provides an N-heteroaryl-4-(haloalkyl)nicotinamide derivative represented by general formula (I):

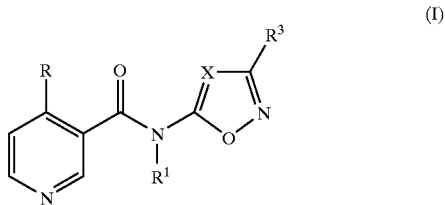

[wherein R represents a $C_1-C_6$ alkyl group which may be substituted with a halogen atom; $R^1$ represents a hydrogen atom, a $C_1-C_6$ alkyl group which may be substituted, a $C_2-C_6$ alkenyl group or an acyl group; X represents a group represented by formula C—$R^2$, or a nitrogen atom; $R^2$ and $R^3$ each independently represent a hydrogen atom, a halogen atom, a $C_1-C_6$ alkyl group which may be substituted with a substituent selected from the following substituent group A, a $C_3-C_7$ cycloalkyl group, a $C_2-C_6$ alkenyl group, a $C_3-C_7$ cycloalkenyl group, a formyl group, a group represented by formula CH=$NOR^4$ (wherein $R^4$ is a hydrogen atom or a $C_1-C_6$ alkyl group), a cyano group, a phenyl group which may be substituted with a substituent selected from the following substituent group B, a 5- or 6-membered heterocyclic group which may be substituted with a substituent selected from the following substituent group B (the heterocycle contains 1 to 3 heteroatoms, which are the same or different, selected from the group consisting of a nitrogen atom, an oxygen atom and a sulfur atom, wherein the number of oxygen atoms and sulfur atoms is 0 or 1), a $C_1-C_6$ alkoxy group which may be substituted with a substituent selected from the following substituent group A, a $C_1-C_6$ alkylthio group or a phenoxy group which may be substituted with a substituent selected from the following substituent group B; substituent group A is a group consisting of a halogen atom, a $C_1-C_6$ alkoxy group, a $C_1-C_6$ alkylthio group, a cyano group and a phenyl group; and substituent group B is a group consisting of a halogen atom, a $C_1-C_6$ alkyl group which may be substituted with a substituent selected from the above substituent group A, a $C_1-C_6$ alkoxy group which may be substituted with a substituent selected from the above substituent group A, a cyano group and a nitro group]; or a salt thereof; and a pesticide containing the N-heteroaryl-4-(haloalkyl)nicotinamide derivative or a salt thereof as an active component.

In the present invention, "a $C_1-C_6$ alkyl group" is a straight or branched chain alkyl group having from 1 to 6 carbon atoms. The group may include, for example, a methyl, ethyl, propyl, isopropyl, butyl, isobutyl, sec-butyl, tert-butyl, pentyl, 2-methylbutyl, 1-methylpentyl, neopentyl, 1-ethylpropyl, hexyl, 1-methylpentyl, 3,3-dimethylbutyl, 2,2-dimethylbutyl or 1,1-dimethylbutyl group, is preferably a straight or branched chain alkyl group having from 1 to 4 carbon atoms (a $C_1$–$C_4$ alkyl group), more preferably an alkyl group having 1 or 2 carbon atoms (a $C_1$–$C_2$ alkyl group), and still more preferably a methyl group.

In the present invention, the "halogen atom" includes, for example, a fluorine atom, a chlorine atom, a bromine atom or an iodine atom, and is preferably a fluorine atom, a chlorine atom or a bromine atom. In $R^2$, a chlorine atom or a bromine atom is more preferred, and in other substituent; a fluorine atom or a chlorine atom is more preferred. In $R^3$, a chlorine atom is still more preferred and in other substituent, a fluorine atom is still more preferred.

In the present invention, the "$C_1$–$C_6$ alkyl group which may be substituted with a halogen atom" is the above "$C_1$–$C_6$ alkyl group" which may be substituted with 1 to 5 "halogen atoms" as defined above, which are the same or different. The group is preferably a methyl group which may be substituted with 1 to 3 fluorine atoms and more preferably a trifluoromethyl group.

In the present invention, the "$C_1$–$C_6$ alkoxy group" is a straight or branched chain alkoxy group having from 1 to 6 carbon atoms. The group may include, for example, a methoxy, ethoxy, isopropoxy, tert-butoxy or hexyloxy group, preferably a straight or branched chain alkoxy group having from 1 to 4 carbon atoms (a $C_1$–$C_4$ alkoxy group), more preferably a straight or branched chain alkoxy group having from 1 to 3 carbon atoms (a $C_1$–$C_3$ alkoxy group), still more preferably a straight chain alkoxy group having 1 or 2 carbon atoms (a $C_1$–$C_2$ alkoxy group), and particularly preferably a methoxy group.

In the present invention, the "$C_1$–$C_6$ alkylthio group" is a straight or branched chain alkylthio group having from 1 to 6 carbon atoms. The group may include, for example, a methylthio, ethylthio, isopropylthio, tert-butylthio or hexylthio group, is preferably a straight or branched chain alkylthio group having from 1 to 4 carbon atoms (a $C_1$–$C_4$ alkylthio group), more preferably a straight or branched chain alkylthio group having from 1 to 3 carbon atoms (a $C_1$–$C_3$ alkylthio group), still more preferably a straight chain alkylthio group having 1 or 2 carbon atoms (a $C_1$–$C_2$ alkylthio group), and particularly preferably a methylthio group.

In the present invention, the "$C_1$–$C_6$ alkyl group which may be substituted with a substituent selected from substituent group A" is the "$C_1$–$C_6$ alkyl group" which may be substituted with 1 to 5 substituents, which are the same or different, selected from the group consisting of the "halogen atom", the "$C_1$–$C_6$ alkoxy group", the "$C_1$–$C_6$ alkylthio group", a cyano group and a phenyl group. In addition to the "$C_1$–$C_6$ alkyl group", the group may include, for example, fluoromethyl, difluoromethyl, trifluoromethyl, pentafluoroethyl, chloromethyl, bromomethyl, iodemethyl, methoxymethyl, methoxyethyl, methoxypropyl, methoxybutyl, methoxypentyl, methoxyhexyl, ethoxymethyl, ethoxyethyl, ethoxypropyl, isopropoxymethyl, isopropoxyethyl, tert-butoxymethyl, tert-butoxyethyl, hexyloxyhexyl, methylthiomethyl, methylthioethyl, methylthiopropyl, methylthiobutyl, methylthiopentyl, methylthiohexyl, ethylthiomethyl, ethylthioethyl, ethylthiopropyl, isopropylthiomethyl, isopropylthioethyl, tert-butylthiomethyl, cyanomethyl, 2-cyanoethyl, 3-cyanopropyl, 4-cyanobutyl, 5-cyanopentyl, 6-cyanohexyl, 1-cyanoethyl, 1-cyanopropyl, 1-cyanoisopropyl or benzyl. In $R^1$, preferred is the "$C_1$–$C_4$ alkyl group" which may be substituted with the "$C_1$–$C_4$ alkoxy group", the "$C_1$–$C_4$ alkylthio group" or a cyano group, more preferred is the "$C_1$–$C_2$ alkyl group" which may be substituted with the "$C_1$–$C_2$ alkoxy group", the "$C_1$–$C_2$ alkylthio group" or a cyano group, and still more preferred is a methyl group, a methoxymethyl group, an ethoxymethyl group or a cyanomethyl group. In $R^2$ and $R^3$, preferred is the "$C_1$–$C_4$ alkyl group" which may be substituted with the "$C_1$–$C_4$ alkoxy group", more preferred is the "$C_1$–$C_3$ alkyl group" which may be substituted with the "$C_1$–$C_3$ alkoxy group", still more preferred is the "$C_1$–$C_2$ alkyl group" which may be substituted with the "$C_1$–$C_2$ alkoxy group", particularly preferred is a methyl group or a methoxymethyl group, and most preferred is a methyl group. In other substituent, preferred is the "$C_1$–$C_4$ alkyl group which may be substituted with 1 to 3 substituents, which are the same or different, selected from the group consisting of a fluorine atom and a chlorine atom, more preferred is the "$C_1$–$C_2$ alkyl group" which may be substituted with 1 to 3 fluorine atoms, and still more preferred is a methyl group or a trifluoromethyl group.

In the present invention, the "$C_2$–$C_6$ alkenyl group" is a straight or branched chain alkenyl group having from 2 to 6 carbon atoms. The group may include, for example, vinyl, 2-chlorovinyl, 2-propenyl, 2-chloro-2-propenyl, 3-chloro-2-propenyl, 3,3-dichloro-2-propenyl, 1-methyl-2-propentyl, 2-methyl-2-propenyl, 1-butenyl, 2-butenyl, 3-methyl-2-butenyl, 1-methyl-2-butenyl, 3-butenyl, 1-pentenyl, 2-pentenyl, 1-hexenyl or 5-hexenyl group, preferably a straight or branched chain alkenyl group having from 2 to 4 carbon atoms (a $C_2$–$C_4$ alkenyl group), more preferably a straight or branched chain alkenyl group having 3 or 4 carbon atoms (a $C_3$–$C_4$ alkenyl group), and still more preferably a 2-propenyl group.

In the present invention, the "acyl group" may include an alkylcarbonyl group which may be substituted (the substituent is, for example, a halogen atom or a lower alkoxy group), an aliphatic acyl group such as an unsaturated alkylcarbonyl group, etc., an arylcarbonyl group which may be substituted (the substituent is, for example, a halogen atom, a lower alkyl group, a lower alkoxy group, a nitro group, a lower alkoxycarbonyl group or an aryl group), a lower alkoxycarbonyl group which may be substituted (the substituent is, for example, a halogen atom or a tri- lower alkylsilyl group), an alkenyloxycarbonyl group; an aralkyloxycarbonyl group which may be substituted (the substituent is, for example, a lower alkoxy group or a nitro group), a lower alkanesulfonyl group which may be substituted (the substituent is, for example, a halogen atom or a lower alkoxy group) and an arylsulfonyl group which may be substituted (the substituent is, for example, a halogen atom, a lower alkyl group, a lower alkoxy group, a nitro group, a lower alkoxycarbonyl group or an aryl group), is preferably an aliphatic acyl group, more preferably a $C_2$–$C_5$ alkylcarbonyl group, and still more preferably an acetyl group.

In the present invention, the "$C_3$–$C_7$ cycloalkyl group" is a cyclic alkyl group having from 3 to 7 carbon atoms. The group may include, for example, a cyclopropyl, cyclobutyl, cyclopentyl, cyclohexyl or cycloheptyl group, is preferably a cyclic alkyl group having from 3 to 6 carbon atoms (a $C_3$–$C_6$ cycloalkyl group), more preferably a cyclic alkyl group having from 3 to 5 carbon atoms (a $C_3$–$C_5$ cycloalkyl group), and still more preferably a cyclopropyl group.

In the present invention, the "$C_3$–$C_7$ cycloalkenyl group" is a cyclic alkenyl group having from 3 to 7 carbon atoms. The group may include, for example, a cyclopropenyl, cyclobutenyl or cyclohexenyl group, is preferably a cyclic alkenyl group having from 3 to 6 carbon atoms (a $C_3$–$C_6$ cycloalkenyl group), and more preferably a cyclohexenyl group.

In the present invention, the "$C_1$–$C_6$ alkoxy group which may be substituted with a substituent selected from substituent group A" is the "$C_1$–$C_6$ alkoxy group" which may be substituted with 1 to 5 substituents, which are the same or different, selected from the group consisting of the "halogen atom", the "$C_1$–$C_6$ alkoxy group", the "$C_1$–$C_6$ alkylthio group", a cyano group and a phenyl group. In addition to the "$C_1$–$C_6$ alkoxy group", the group may include, for example, fluoromethoxy, difluoromethoxy, trifluoromethoxy, pentafluoroethoxy, chloromethoxy, bromomethoxy, iodemethoxy, methoxymethoxy, methoxyethoxy, methoxypropoxy, methoxybutoxy, methoxypentoxy, methoxyhexyloxy, ethoxymethoxy, ethoxyethoxy, ethoxypropoxy, isopropoxymethoxy, isopropoxyethoxy, tert-butoxymethoxy, tert-butoxyethoxy, hexyloxyhexyloxy, methylthiomethoxy, methylthioethoxy, methylthiopropoxy, methylthiobutoxy, methylthiopentoxy, methylthiohexyloxy, ethylthiomethoxy, ethylthioethoxy, ethylthiopropoxy, isopropylthiomethoxy, isopropylthioethoxy, tert-butylthiomethoxy, cyanomethoxy, 2-cyanoethoxy, 3-cyanopropoxy, 4-cyanobutoxy, 5-cyanopentoxy, 6-cyanohexyloxy, 1-cyanoethoxy, 1-cyanopropoxy, 1-cyanoisopropyloxy or benzyloxy, is preferably the "$C_1$–$C_4$ alkoxy group" which may be substituted with 1 to 3 substituents, which are the same or different, selected from the group consisting of a fluorine atom and a chlorine atom, more preferably the "$C_1$–$C_2$ alkoxy group" which may be substituted with 1 to 3 fluorine atoms, and still more preferably a methoxy group or a trifluoromethoxy group.

In the present invention, the "phenyl group which may be substituted with a substituent selected from substituent group B" is a phenyl group which may be substituted with 1 to 5 substituents, which are the same or different, selected from the group consisting of the "halogen atom", the "$C_1$–$C_6$ alkyl group which may be substituted with a substituent selected from substituent group A", the "$C_1$–$C_6$ alkoxy group which may be substituted with a substituent selected from substituent group A", a cyano group and a nitro group. In $R^2$, preferred is a phenyl group which may be substituted with 1–3 substituents, which are the same or different, selected from the group consisting of a fluorine atom, a chlorine atom, the "$C_1$–$C_4$ alkyl group" which may be substituted (the substituent is a fluorine atom or a chlorine atom), the "$C_1$–$C_4$ alkoxy group" which may be substituted (the substituent is a fluorine atom or a chlorine atom), a cyano group and a nitro group, more preferred is a phenyl group which may be substituted with 1 to 3 substituents, which are the same or different, selected from the group consisting of a fluorine atom, a chlorine atom, the "$C_1$–$C_3$ alkyl group" which may be substituted (the substituent is a fluorine atom), the "$C_1$–$C_2$ alkoxy group" which may be substituted (the substituent is a fluorine atom), a cyano group and a nitro group, and still more preferred is a phenyl group. In other substituent, preferred is a phenyl group which may be substituted with 1 to 3 substituents, which are the same or different, selected from the group consisting of a fluorine atom, a chlorine atom, a bromine atom, the "$C_1$–$C_4$ alkyl group" which may be substituted (the substituent is a fluorine atom or a chlorine atom), the "$C_1$–$C_4$ alkoxy group", a cyano group and a nitro group, more preferred is a phenyl group which may be substituted with 1 to 3 substituents, which are the same or different, selected from the group consisting of a fluorine atom, a chlorine atom, the "$C_1$–$C_2$ alkyl group" which may be substituted (the substituent is a fluorine atom), the "$C_1$–$C_2$ alkoxy group", a cyano group and a nitro group, and still more preferred is a phenyl group.

In the present invention, the "5- or 6-membered heterocyclic group (the heterocycle contains 1 to 3 heteroatoms, which are the same or different, selected from the group consisting of a nitrogen atom, an oxygen atom and a sulfur atom, wherein the number of oxygen atoms and sulfur atoms is 0 or 1)" may include, for example, pyridyl, pyrimidinyl, pyridazinyl, pyrazinyl, triazinyl, pyrrolyl, furyl, thienyl, pyrazolyl, imidazolyl, oxazolyl, isoxazolyl, thiazolyl, isothiazolyl, triazolyl, oxadiazolyl or thiadiazolyl, preferably a 5- or 6-membered heterocyclic group in which heteroatoms in the ring are 1 to 3 nitrogen atoms {5- or 6-membered heterocyclic group (the heterocycle contains 1 to 3 nitrogen atoms)}, and more preferably a pyridyl group or a pyrazolyl group.

In the present invention, the "5- or 6-membered heterocyclic group which may be substituted with a substituent selected substituent group B (the heterocycle contains 1 to 3 heteroatoms, which are the same or different, selected from the group consisting of a nitrogen atom, an oxygen atom and a sulfur atom, wherein the number of oxygen atoms and sulfur atoms is 0 or 1)" is the "5- or 6-membered heterocyclic group (the heterocycle contains 1 to 3 heteroatoms, which are the same or different, selected from the group consisting of a nitrogen atom, an oxygen atom and a sulfur atom, wherein the number of oxygen atoms and sulfur atoms is 0 or 1)" which may be substituted with 1 to 4 substituents, which are the same or different, selected from the group consisting of the "halogen atom", the "$C_1$–$C_6$ alkyl group which may be substituted with a substituent selected from substituent group A", the "$C_1$–$C_6$ alkoxy group which may be substituted with a substituent selected from substituent group A", a cyano group or a nitro group, preferably the 5- or 6-membered heterocyclic group (the heterocycle contains 1 to 3 nitrogen atoms) which may be substituted with 1 to 3 substituents, which are the same or different, selected from the group consisting of a fluorine atom, a chlorine atom, the "$C_1$–$C_4$ alkyl group" which may be substituted (the substituent is a fluorine atom or a chlorine atom), the "$C_1$–$C_4$ alkoxy group" which may be substituted (the substituent is a fluorine atom or a chlorine atom), a cyano group and a nitro group, more preferably a pyridyl group or pyrazolyl group which may be substituted with 1 or 2 substituents, which are the same or different, selected from the group consisting of a fluorine atom, a chlorine atom and the $C_1$–$C_3$ alkyl group, and still more preferably a pyridyl group or a pyrazolyl group.

In the present invention, the "phenoxy group which may be substituted with a substituent selected from substituent group B" is a phenoxy group which may be substituted with 1 to 5 substituents, which are the same or different, selected from the group consisting of the "halogen atom", the "$C_1$–$C_6$ alkyl group which may be substituted with a substituent selected from substituent group A", the "$C_1$–$C_6$ alkoxy group which may be substituted with a substituent selected from substituent group A", a cyano group and a nitro group, preferably a phenoxy group which may be substituted with 1 to 3 substituents, which are the same or different, selected from the group consisting of a fluorine atom, a chlorine atom, the "$C_1$–$C_4$ alkyl group" which may be substituted (the substituent is a fluorine atom or a chlorine atom), the "$C_1$–$C_4$ alkoxy group" which may be substituted (the substituent is a fluorine atom or a chlorine atom), a cyano group and a nitro group, more preferably a phenoxy group which may be substituted with 1 to 3 substituents, which are the same or different, selected from the group consisting of a fluorine atom, a chlorine atom, the "$C_1$–$C_3$ alkyl group" which may be substituted (the substituent is a fluorine atom), the "$C_1$–$C_2$ alkoxy group" which may be substituted (the substituent is a fluorine atom), a cyano group and a nitro group, and still more preferably a phenoxy group.

(1) In the present invention, R is preferably a trifluoromethyl group.

(2) In the present invention, $R^1$ is preferably a hydrogen atom, a $C_1$–$C_4$ alkyl group which may be substituted (the substituent is the $C_1$–$C_4$ alkoxy, $C_1$–$C_4$ alkylthio or cyano group), a $C_3$–$C_4$ alkenyl group or a $C_2$–$C_5$ alkylcarbonyl group, more preferably a hydrogen atom or a $C_1$–$C_2$ alkyl group which may be substituted (the substituent is the $C_1$–$C_2$ alkoxy, $C_1$–$C_2$ alkylthio or cyano group), still more preferably a hydrogen atom, a methyl group, a methoxymethyl group, an ethoxymethyl group or a cyanomethyl group, and particularly preferably a hydrogen atom.

(3) In the present invention, X is preferably a group represented by formula C—$R^2$.

(4) In the present invention, $R^2$ is preferably a hydrogen atom, a fluorine atom, a chlorine atom, a bromine atom, an iodine atom, a $C_1$–$C_4$ alkyl group which may be substituted (the substituent is a substituent selected from the group consisting of a fluorine atom, a chlorine atom, a $C_1$–$C_4$ alkoxy group and a phenyl group), a $C_3$–$C_6$ cycloalkyl group, a $C_2$–$C_4$ alkenyl group, a $C_3$–$C_6$ cycloalkenyl group, a phenyl group which may be substituted {the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, a 5- or 6-membered heterocyclic group which may be substituted {the heterocycle contains 1 to 3 nitrogen atoms, the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, a $C_1$–$C_4$ alkoxy group which may be substituted (the substituent is a substituent selected from the group consisting of a fluorine atom, a chlorine atom, a $C_1$–$C_4$ alkoxy group and a phenyl group), a $C_1$–$C_4$ alkylthio group or a phenoxy group which may be substituted {the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, more preferably a hydrogen atom, a fluorine atom, a chlorine atom, a bromine atom, an iodine atom, a $C_1$–$C_3$ alkyl group which may be substituted (the substituent is a $C_1$–$C_3$ alkoxy group), a $C_3$–$C_5$ cycloalkyl group, a $C_3$–$C_4$ alkenyl group, a phenyl group which may be substituted (the substituent is a substituent selected from the group consisting of a fluorine atom, a chlorine atom, a $C_1$–$C_3$ alkyl group which may be substituted with a fluorine atom, a $C_1$–$C_3$ alkoxy group which may be substituted with a fluorine atom, a cyano group and a nitro group), a pyridyl group which may be substituted (the substituent is a substituent selected from the group consisting of a fluorine atom, a chlorine atom and a $C_1$–$C_3$ alkyl group), a pyrazolyl group which may be substituted (the substituent is a substituent selected from the group consisting of a fluorine atom, a chlorine atom and a $C_1$–$C_3$ alkyl group), a $C_1$–$C_3$ alkoxy group which may be substituted with a fluorine atom, a $C_1$–$C_3$ alkylthio group or a phenoxy group which may be substituted (the substituent is a substituent selected from the group consisting of a fluorine atom, a chlorine atom, a $C_1$–$C_3$ alkyl group which may be substituted with a fluorine atom, a $C_1$–$C_3$ alkoxy group which may be substituted with a fluorine atom, a cyano group and a nitro group), still more preferably a hydrogen atom, a fluorine atom, a chlorine atom, a bromine atom, a $C_1$–$C_3$ alkyl group, a cyclopropyl group, an allyl group, a phenyl group, a pyridyl group, a pyrazolyl group, a $C_1$–$C_2$ alkoxy group, a $C_1$–$C_2$ alkylthio group or a phenoxy group, and particularly preferably a hydrogen atom, a chlorine atom, a bromine atom, a methyl group, an ethyl group or a methoxy group.

(5) In the present invention, $R^3$ is preferably a hydrogen atom, a fluorine atom, a chlorine atom, a bromine atom, a $C_1$–$C_4$ alkyl group which may be substituted (the substituent is a $C_1$–$C_4$ alkoxy group), a $C_3$–$C_6$ cycloalkyl group, a formyl group, a group represented by formula CH=NOR$^{4a}$ (wherein $R^{4a}$ is a hydrogen atom or a $C_1$–$C_4$ alkyl group), a cyano group or a phenyl group which may be substituted {the substituents are 1 to 3 substituents, which are the same or different, selected from the group consisting of a fluorine atom, a chlorine atom, a bromine atom, a $C_1$–$C_4$ alkyl group which may be substituted (the substituent is a fluorine atom or a chlorine atom), a $C_1$–$C_4$ alkoxy group, a cyano group and a nitro group, more preferably a hydrogen atom, a fluorine atom, a chlorine atom, a $C_1$–$C_2$ alkyl group which may be substituted (the substituent is a $C_1$–$C_2$ alkoxy group), a $C_3$–$C_5$ cycloalkyl group or a phenyl group which may be substituted {the substituents are 1 to 3 substituents, which are the same or different, selected from the group consisting of a fluorine atom, a chlorine atom, a $C_1$–$C_2$ alkyl group which may be substituted (the substituent is a fluorine atom), a $C_1$–$C_2$ alkoxy group, a cyano group and a nitro group}, still more preferably a hydrogen atom, a chlorine atom, a methyl group, a methoxymethyl group, a cyclopropyl group or a phenyl group, and particularly preferably a hydrogen atom or a methyl group.

The 4-(haloalkyl)nicotinamide derivative of the present invention is preferably a compound in which:

(a1) R is a trifluoromethyl group, (a2) $R^1$ is a hydrogen atom, a $C_1$–$C_4$ alkyl group which may be substituted (the substituent is a $C_1$–$C_4$ alkoxy group, a $C_1$–$C_4$ alkylthio group or a cyano group), a $C_3$–$C_4$ alkenyl group or a $C_2$–$C_5$ alkylcarbonyl group, (a3) X is a group represented by formula C—$R^2$, (a4) $R^2$ is a hydrogen atom, a fluorine atom, a chlorine atom, a bromine atom, an iodine atom, a $C_1$–$C_4$ alkyl group which may be substituted (the substituent is a substituent selected from the group consisting of a fluorine atom, a chlorine atom, a $C_1$–$C_4$ alkoxy group and a phenyl group), a $C_3$–$C_6$ cycloalkyl group, a $C_2$–$C_4$ alkenyl group, a $C_3$–$C_6$ cycloalkenyl group, a phenyl group which may be substituted {the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, a 5- or 6-membered heterocyclic group which may be substituted {the heterocycle contains 1 to 3 nitrogen atoms, and the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, a $C_1$–$C_4$ alkoxy group which may be substituted (the substituent is a substituent selected from the group consisting of a fluorine atom, a chlorine atom, a $C_1$–$C_4$ alkoxy group and a phenyl group), a $C_1$–$C_4$ alkylthio group or a phenoxy group which may be substituted {the substituent is a substituent selected from the group consisting of a fluorine atom, a chlorine atom, a $C_1$–$C_4$ alkyl group which may be substituted (the substituent is a fluorine atom or a chlorine atom), a $C_1$–$C_4$ alkoxy group which may be substituted (the substituent is a fluorine atom or a chlorine atom), a cyano group and a nitro group}, and (a5) $R^3$ is a hydrogen atom, a fluorine atom, a chlorine atom, a bromine atom, a $C_1$–$C_4$ alkyl group which may be substituted (the substituent is a $C_1$–$C_4$ alkoxy group), a $C_3$–$C_6$ cycloalkyl group, a formyl group, a group represented by formula CH=NOR$^{4a}$ (wherein R$^{4a}$ is a hydrogen atom or a $C_1$–$C_4$ alkyl group), a cyano group or a phenyl group which may be substituted {the substituents are 1–3 substituents, which are the same or different, selected from the group consisting of a fluorine atom, a chlorine atom, a bromine atom, a $C_1$–$C_4$ alkyl group which may be substituted (the substituent is a fluorine atom or a chlorine atom), a $C_1$–$C_4$ alkoxy group, a cyano group and a nitro group}, more preferably a compound in which:

(b1) R is a trifluoromethyl group, (b2) $R^1$ is a hydrogen atom or a $C_1$–$C_2$ alkyl group which may be substituted (the substituent is a $C_1$–$C_2$ alkoxy, $C_1$–$C_2$ alkylthio or cyano group), (b3) X is a group represented by formula C—R$^2$, (b4) $R^2$ is a hydrogen atom, a fluorine atom, a chlorine atom, a bromine atom, an iodine atom, a $C_1$–$C_3$ alkyl group which may be substituted (the substituent is a $C_1$–$C_3$ alkoxy group), a $C_3$–$C_5$ cycloalkyl group, a $C_3$–$C_4$ alkenyl group, a phenyl group which may be substituted (the substituent is a substituent selected from the group consisting of a fluorine atom, a chlorine atom, a $C_1$–$C_3$ alkyl group which may be substituted with a fluorine atom, a $C_1$–$C_3$ alkoxy group which may be substituted with a fluorine atom, a cyano group and a nitro group), a pyridyl group which may be substituted (the substituent is a substituent selected from the group consisting of a fluorine atom, a chlorine atom and a $C_1$–$C_3$ alkyl group), a pyrazolyl group which may be substituted (the substituent is a substituent selected from the group consisting of a fluorine atom, a chlorine atom and a $C_1$–$C_3$ alkyl group), a $C_1$–$C_3$ alkoxy group which may be substituted with a fluorine atom, a $C_1$–$C_3$ alkylthio group or a phenoxy group which may be substituted (the substituent is a substituent selected from the group consisting of a fluorine atom, a chlorine atom, a $C_1$–$C_3$ alkyl group which may be substituted with a fluorine atom, a $C_1$–$C_3$ alkoxy group which may be substituted with a fluorine atom, a cyano group and a nitro group), and (b5) $R^3$ is a hydrogen atom, a fluorine atom, a chlorine atom, a $C_1$–$C_2$ alkyl group which may be substituted (the substituent is a $C_1$–$C_2$ alkoxy group), a $C_3$–$C_5$ cycloalkyl group or a phenyl group which may be substituted {the substituents are 1 to 3 substituents, which are the same or different, selected from the group consisting of a fluorine atom, a chlorine atom, a $C_1$–$C_2$ alkyl group which may be substituted (the substituent is a fluorine atom), a $C_1$–$C_2$ alkoxy group, a cyano group and a nitro group}, still more preferably a compound in which:

(c1) R is a trifluoromethyl group, (c2) $R^1$ is a hydrogen atom, a methyl group, a methoxymethyl group, an ethoxymethyl group or a cyanomethyl group, (c3) X is a group represented by formula C—R$^2$, (c4) $R^2$ is a hydrogen atom, a fluorine atom, a chlorine atom, a bromine atom, a $C_1$–$C_3$ alkyl group, a cyclopropyl group, an allyl group, a phenyl group, a pyridyl group, a pyrazolyl group, a $C_1$–$C_2$ alkoxy group, a $C_1$–$C_2$ alkylthio group or a phenoxy group, and (c5) $R^3$ is a hydrogen atom, a chlorine atom, a methyl group, a methoxymethyl group, a cyclopropyl group or a phenyl group, particularly preferably a compound in which:

(d1) R is a trifluoromethyl group, (d2) $R^1$ is a hydrogen atom, (d3) X is a group represented by formula C—R$^2$, (d4) $R^2$ is a hydrogen atom, a chlorine atom, a bromine atom, a methyl group, an ethyl group or a methoxy group, and (d5) $R^3$ is a hydrogen atom or a methyl group, and most preferably (e) N-(5-isoxazolyl)-4-(trifluromethyl)nicotinamide,
N-(3-methyl-5-isoxazolyl)-4-(trifluoromethyl)nicotinamide,
N-(4-chloro-5-isoxazolyl)-4-(trifluoromethyl)nicotinamide,
N-(4-bromo-5-isoxazolyl)-4-(trifluoromethyl)nicotinamide,
N-(4-methyl-5-isoxazolyl)-4-(trifluromethyl)nicotinamide,
N-(4-ethyl-5-isoxazolyl)-4-(trifluoromethyl)nicotinamide or
N-(4-methoxy-5-isoxazolyl)-4-(trifluoromethyl)nicotinamide.

The N-heteroaryl-4-(haloalkyl)nicotinamide derivative of the present invention may form a salt with an acidic substance or a basic substance. For example, when a dissociable proton is present in a molecule, alkali metal salts, alkali earth metal salts or ammonium salts can be formed. Further, as salts with acidic substances, salts such as sulfate, hydrochloride, nitrate and phosphate can be formed. These salts are included in the present invention as long as they can be used as an insecticide for agriculture and horticulture.

In the present invention, the "alkali metal salts" may include, for example, sodium salts, potassium salts or lithium salts and are preferably sodium salts or potassium salts.

In the present invention, the "alkali earth metal salts" may include, for example, calcium salts or magnesium salts and are preferably calcium salts.

Solvates (preferably hydrates) of the N-heteroaryl-4-(haloalkyl)nicotinamide derivative of the present invention are also included in the present invention.

In the N-heteroaryl-4-(haloalkyl)nicotinamide derivative of the present invention, compounds having an asymmetric carbon are also included. In this case, the present invention includes one kind of optically active substance and a mixture of several kinds of optically active substances at any ratio.

The representative compounds of the present invention are exemplified in the following Tables 1 and 2, however, the present invention is not limited to these compounds.

In the following tables, "Me" represents a methyl group, "Et" represents an ethyl group, "Pr" represents a propyl group, "iPr" represents an isopropyl group, "cPr" represents a cyclopropyl group, "Bu" represents a butyl group, "Pent" represents a pentyl group, "Hex" represents a hexyl group, "Ph" represents a phenyl group, "4-CF$_3$-Ph" represents 4-trifluoromethylphenyl group, "CHO" represents a formyl group, "Ac" represents an acetyl group, "4-CF$_3$-Py-3-yl" represents a 4-trifluoromethyl-3-pyridyl group, "iBu" represents an isobutyl group, "cBu" represents a cyclobutyl group, "cPent" represents a cyclopentyl group, "cHex-1-en-1-yl" represents a 1-cyclohexenyl group and "1-Pyza" represents a 1-pyrazolyl group, respectively.

TABLE 1

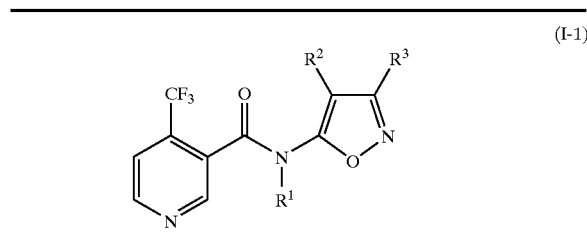

(I-1)

| Compound No. | R¹ | R² | R³ |
|---|---|---|---|
| 1-1 | H | H | H |
| 1-2 | H | H | Me |
| 1-3 | H | H | Et |
| 1-4 | H | H | Pr |
| 1-5 | H | H | iPr |
| 1-6 | H | H | cPr |
| 1-7 | H | H | Bu |
| 1-8 | H | H | Pent |
| 1-9 | H | H | Hex |
| 1-10 | H | H | Ph |
| 1-11 | H | H | 4-Me—Ph |
| 1-12 | H | H | 4-Cl—Ph |
| 1-13 | H | H | 4-OMe—Ph |
| 1-14 | H | H | 4-CN—Ph |
| 1-15 | H | H | 4-CF₃—Ph |
| 1-16 | H | H | CHO |
| 1-17 | H | H | CH=N—OH |
| 1-18 | H | H | CN |
| 1-19 | H | H | CH₂OMe |
| 1-20 | H | Cl | H |
| 1-21 | H | Cl | Me |
| 1-22 | H | Cl | Et |
| 1-23 | H | Cl | Pr |
| 1-24 | H | Cl | iPr |
| 1-25 | H | Cl | cPr |
| 1-26 | H | Cl | Bu |
| 1-27 | H | Cl | Pent |
| 1-28 | H | Cl | Hex |
| 1-29 | H | Cl | Ph |
| 1-30 | H | Cl | 4-Me—Ph |
| 1-31 | H | Cl | 4-Cl—Ph |
| 1-32 | H | Cl | 4-OMe—Ph |
| 1-33 | H | Cl | 4-CN—Ph |
| 1-34 | H | Cl | 4-CF₃—Ph |
| 1-35 | H | Cl | CH=N—OH |
| 1-36 | H | Cl | CN |
| 1-37 | H | Cl | CH₂OMe |
| 1-38 | H | F | H |
| 1-39 | H | F | Me |
| 1-40 | H | Br | H |
| 1-41 | H | Br | Me |
| 1-42 | H | I | H |
| 1-43 | H | I | Me |
| 1-44 | H | CN | H |
| 1-45 | H | CN | Me |
| 1-46 | Me | H | H |
| 1-47 | Me | H | Me |
| 1-48 | CH₂CH=CH₂ | H | H |
| 1-49 | CH₂CH=CH₂ | H | Me |
| 1-50 | CH₂OEt | H | H |
| 1-51 | CH₂OEt | H | Me |
| 1-52 | CH₂CN | H | H |
| 1-53 | CH₂CN | H | Me |
| 1-54 | CH₂SMe | H | H |
| 1-55 | CH₂SMe | H | Me |
| 1-56 | H | H | CH(OEt)₂ |
| 1-57 | Ac | H | Me |
| 1-58 | H | H | CH=N—OMe |
| 1-59 | H | H | CO₂Et |
| 1-60 | CO(4-CF₃—Py-3-yl) | H | H |
| 1-61 | CH₂OEt | I | H |
| 1-62 | H | Me | H |
| 1-63 | H | Me | Me |
| 1-64 | H | Et | H |
| 1-65 | H | Pr | H |

TABLE 1-continued

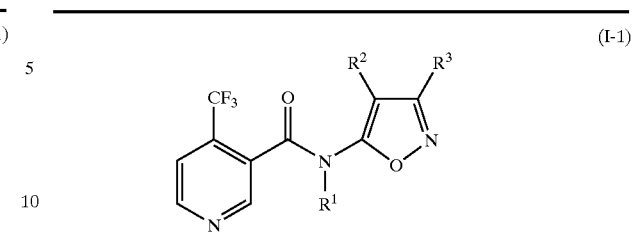

(I-1)

| Compound No. | R¹ | R² | R³ |
|---|---|---|---|
| 1-66 | H | iPr | H |
| 1-67 | H | cPr | H |
| 1-68 | H | CH₂CH=CH₂ | H |
| 1-69 | H | Bu | H |
| 1-70 | H | iBu | H |
| 1-71 | H | cBu | H |
| 1-72 | H | cPent | H |
| 1-73 | H | Hex | H |
| 1-74 | CO(4-CF₃—Py-3-yl) | Hex | H |
| 1-75 | H | CH₂Ph | H |
| 1-76 | H | CH₂CH₂Ph | H |
| 1-77 | H | OMe | H |
| 1-78 | H | OMe | CH₂OMe |
| 1-79 | H | SMe | H |
| 1-80 | CO(4-CF₃—Py-3-yl) | SMe | H |
| 1-81 | H | OPh | H |
| 1-82 | CO(4-CF₃—Py-3-yl) | OPh | H |
| 1-83 | H | Ph | H |
| 1-84 | H | 4-Me—Ph | H |
| 1-85 | H | 4-OMe—Ph | H |
| 1-86 | H | 4-Cl—Ph | H |
| 1-87 | H | 4-CF₃—Ph | H |
| 1-88 | H | 4-OCF₃—Ph | H |
| 1-89 | H | 3-Py | H |
| 1-90 | H | Cl | CH=N—OMe |
| 1-91 | H | Ph | Me |
| 1-92 | H | cHex-1-en-1-yl | H |
| 1-93 | H | CH₂OMe | H |
| 1-94 | H | 1-Pyza | H |
| 1-95 | H | cHex | H |

TABLE 2

(I-2)

| Compound No. | R¹ | R³ |
|---|---|---|
| 2-1 | H | H |
| 2-2 | H | Me |
| 2-3 | H | Et |
| 2-4 | H | Pr |
| 2-5 | H | iPr |
| 2-6 | H | cPr |
| 2-7 | H | Bu |
| 2-8 | H | Pent |
| 2-9 | H | Hex |
| 2-10 | H | Ph |
| 2-11 | H | 4-Me—Ph |
| 2-12 | H | 4-Cl—Ph |
| 2-13 | H | 4-OMe—Ph |

TABLE 2-continued

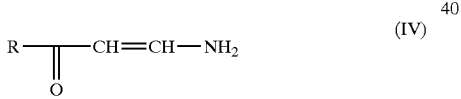
(I-2)

| Compound No. | R¹ | R³ |
|---|---|---|
| 2-14 | H | 4-CN—Ph |
| 2-15 | H | 4-CF$_3$—Ph |

Among the above exemplification compounds, preferable compounds are those of compound Nos.: 1-1, 1-2, 1-3, 1-5, 1-16, 1-17, 1-18, 1-19, 1-20, 1-21, 1-25, 1-36, 1-37, 1-38, 1-39, 1-40, 1-41, 1-42, 1-43, 1-47, 1-49, 1-51, 1-53, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95 and 2-2, more preferably those of compound Nos.: 1-1, 1-2, 1-20, 1-21, 1-37, 1-38, 1-39, 1-40, 1-41, 1-42, 1-43, 1-53, 1-57, 1-60, 1-61, 1-62, 1-64, 1-65, 1-66, 1-67, 1-68, 1-69, 1-70, 1-71, 1-77, 1-78, 1-79, 1-80, 1-81, 1-82, 1-86, 1-89, 1-90, 1-92, 1-93, 1-94 and 2-2, still more preferably those of compound Nos.: 1-1, 1-2, 1-20, 1-21, 1-38, 1-39, 1-40, 1-42, 1-62, 1-64, 1-65, 1-67, 1-77, 1-93 and 1-94, and particularly preferably those of compound Nos.: 1-1, 1-2, 1-20, 1-40, 1-62, 1-64 and 1-77.

Further, the present invention provides a method for producing an N-heteroaryl-4-(haloalkyl)nicotinamide derivative or a salt thereof, comprising reacting an amine compound represented by general formula (IV):

(IV)

[wherein R represents the same meaning as defined above] with an acrylonitrile compound represented by general formula (V):

X$^a$—CH═CH—CN  (V)

[wherein X$^a$ represents a leaving group] or a propionitrile compound represented by general formula (VI):

(R$^a$O)$_2$CH—CH$_2$—CN  (VI)

[wherein R$^a$ represents a hydrogen atom or a C$_1$–C$_6$ alkyl group] to produce a nitrile compound represented by general formula (II):

(II)

[wherein R represents the same meaning as defined above] or a salt thereof, adding a base to the nitrile compound or a salt thereof to produce a 4-substituted pyridine compound having a cyano group, a carbamoyl group or a carboxyl group at position 3, represented by general formula (VII):

(VII)

[wherein R represents the same meaning as defined above, and A represents a cyano group, a carbamoyl group or a carboxyl group], hydrolyzing the 4-substituted pyridine compound by adding thereto an acid or an alkali, if necessary, to produce a carboxylic acid compound represented by general formula (VIII):

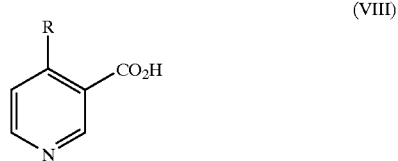
(VIII)

[wherein R represents the same meaning as defined above], reacting a halogenating agent with the carboxylic acid compound to produce an acid halide compound represented by general formula (IX):

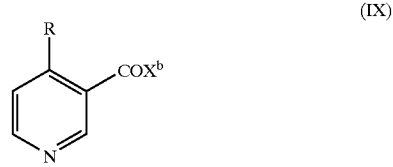
(IX)

[wherein R represents the same meaning as defined above, and X$^b$ represents a chlorine atom or a bromine atom], and reacting an amino compound represented by general formula (III):

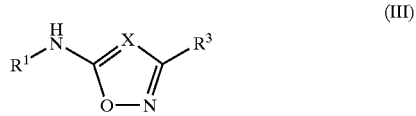
(III)

[wherein R, X, R¹ and R³ represent the same meanings as defined above] with the acid halide compound, further followed by alkylation, alkenylation or acylation, if necessary, to produce an N-heteroaryl-4-(haloalkyl)nicotinamide derivative represented by general formula (I) above:

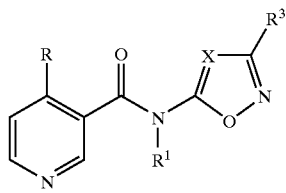

(I)

[wherein R, X, R$^1$ and R$^3$ represent the same meanings as defined above], or a salt thereof. The present invention also provides a nitrile compound represented by general formula (VII):

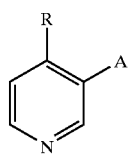

(VII)

[wherein R represents the same meaning as defined above] or a salt thereof, which is an intermediate for the production of compound (I).

In the present invention, the "leaving group" is not particularly limited as long as it is a functional group having a leaving ability. The group may include, for example, a halogen atom, a $C_1$–$C_6$ alkoxy group, a phenoxy group or a cyano group, is preferably a chlorine atom, a methoxy or ethoxy group, and more preferably a methoxy group.

In the present invention, R$^a$ is preferably a straight or branched chain alkyl group having from 1 to 3 carbon atoms, more preferably a methyl or ethyl group and still more preferably a methyl group.

Compound (II) of the present invention can form, for example, alkali metal salts, alkali earth metal salts or ammonium salts.

The solvates (preferably hydrates) of compound (II) of the present invention are also included in the present invention.

In the present invention, an optical isomer may be present in each of compound (II), compound (IV), compound (V), compound (VI), compound (VII), compound (VIII) and compound (IX). The compounds of the present invention each include one kind of optically active substance and a mixture of several kinds of optically active substances at an arbitrary ratio.

In the production method of the present invention, compound (IV) to be used is a commercially available one or can be produced by a known method (for example, a method described in Tetrahedron Letters, 1989, 30, 6173–6176, US Patent Publication 2198260, Arch. Pharm., 1984, 317, 156–162 or Izv. Akad. Nauk. SSSR. Ser. Khim., 1955, 179).

In the production method of the present invention, compound (V) to be used is a commercially available one or can be produced by a known method (for example, when X is an alkoxy group, used is a method described in J. Am. Chem, Soc., 1947, 69, 2660 or Kogyo Kagaku Zasshi, 1970, 73, 1013; and when X is a chlorine atom, used is a method described in J. Org. Chem., 1964, 29, 1800–1808, J. Org. Chem., 1970, 35, 2133 or Collect. Czech. Chem. Commun., 1983, 48, 89–95).

In the production method of the present invention, compound (VI) to be used is a commercially available one or can be produced by a known method (for example, when R$^1$ is a butoxy group, used is a method described in J. Chem. Soc. Chem. Commun., 1977, 333).

The N-heteroaryl-4-(haloalkyl)nicotinamide derivative of the present invention can be produced by steps A to C described below.

(Step A)

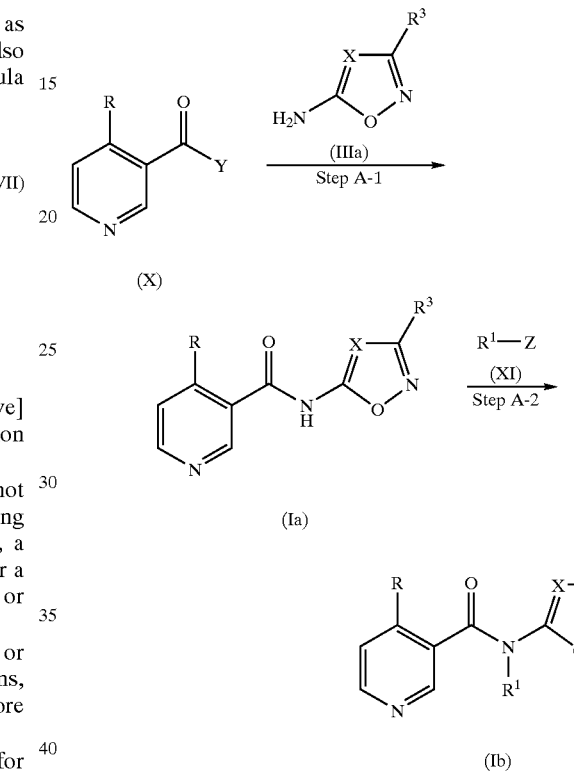

In the formula, R, R$^1$, X and R$^3$ represent the same meanings as defined above, Y represents a hydroxyl group or a halogen atom (preferably a chlorine atom), and Z represents a leaving group (preferably a halogen atom such as chlorine, bromine and iodine; a trihalogenomethyloxy group such as trichloromethyloxy; a lower alkanesulfonyloxy group such as methanesulfonyloxy and ethanesulfonyloxy; a halogeno lower alkanesulfonyloxy group such as trifluoromethanesulfonyloxy and pentafluoroethanesulfonyloxy, or an arylsulfonyloxy group such as benzenesulfonyloxy, p-toluenesulfonyloxy and p-nitrobenzenesulfonyloxy).

(Step A-1)

Step A-1 is a step of reacting a 4-(haloalkyl)pyridine-3-carboxylic acid represented by general formula (X) or an acid halide thereof with an amine compound represented by general formula (IIIa) or a salt thereof to produce compound (Ia) of the present invention.

When Y in compound (X) is a hydroxyl group, this is a step of reacting compound (IIIa) with compound (X) in an inactive solvent in the presence of a base and a condensing agent to produce compound (Ia).

In this step, the base used is not particularly limited as long as it is a base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; metal hydrides such as sodium hydride and potassium hydride; alkoxides such as sodium methoxide, sodium ethoxide and potassium tert-butoxide; organic bases such as triethylamine, N,N-dimethylaniline and pyridine; or organometallics such as methyllithium, butyllithium, methylmagnesium bromide and lithium diisopropylamide, is preferably alkali metal carbonates, alkali metal bicarbonates or organic bases, and more preferably sodium carbonate, potassium carbonate, pyridine or triethylamine.

The amount of the base used is usually from 1.0 to 10.0 mol, preferably from 1.0 to 5.0 mol based on 1 mol of compound (X).

The condensing agent used is not particularly limited as long as it is a reagent having a condensing ability. The agent may include, for example, $C_1$–$C_4$ alkyl chloroformate such as methyl chloroformate and ethyl chloroformate, pyridinium salts such as 2-chloro-1-methylpyridinium iodide; and carbodiimides such as dicyclohexylcarbodiimide, is preferably pyridinium salts, and more preferably 2-chloro-1-methylpyridinium iodide.

The amount of the condensing agent used is usually from 1.0 to 5.0 mol, preferably from 1.0 to 2.0 mol based on 1 mol of compound (X).

The solvent used is not particularly limited as long as it does not inhibit the reaction and dissolves the starting material to some extent. The solvent may include, for example, ethers such as diethyl ether, dimethoxyethane, tetrahydrofuran, and dioxane; aromatic hydrocarbons such as benzene, toluene, xylene and chlorobenzene; nitrites such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably ethers, halogenated hydrocarbons, esters, aliphatic hydrocarbons or aromatic hydrocarbons, and more preferably tetrahydrofuran, methylene chloride, ethyl acetate or toluene.

The amount of the solvent used is usually from 1.0 to 20 liter and preferably from 1.0 to 10 liter, based on 1 mol of compound (X).

The reaction temperature varies depending on the starting compound, the reagent and the solvent, however, it is usually from –40° C. to 150° C. and preferably from 0° C. to 100° C.

The reaction time varies depending on the starting compound, the reagent, the solvent, the reaction temperature and the like, however, it is usually from 6 minutes to 48 hours and preferably from 10 minutes to 24 hours.

(ii) When Y in compound (X) is a halogen atom, this step is a step of reacting compound (IIIa) with compound (X) in an inactive solvent in the presence of a base to produce compound (Ia).

The base used is not particularly limited as long as it is a base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; metal hydride such as sodium hydride and potassium hydride; alkoxides such as sodium methoxide, sodium ethoxide and potassium tert-butoxide; organic bases such as triethylamine, N,N-dimethylaniline and pyridine; or organometallics such as methyllithium, butyllithium, methylmagnesium bromide and lithium diisopropylamide; is preferably alkali metal carbonates, alkali metal bicarbonates or organic bases; and more preferably sodium carbonate, sodium bicarbonate, pyridine or triethylamine.

The solvent used is not particularly limited as long as it does not inhibit the reaction and dissolves the starting material to some extent. The solvent may include, for example, ethers such as diethyl ether, dimethoxyethane, tetrahydrofuran, and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably ethers, halogenated hydrocarbons, esters, aliphatic hydrocarbons or aromatic hydrocarbons, and more preferably tetrahydrofuran, ethyl acetate or toluene. Further, in this step, two-phase reaction may be carried out using the nonaqueous solvent and water.

The amount of the solvent used is usually from 1.0 to 20 liter, preferably from 1.0 to 10 liter based on 1 mol of compound (IIIa).

The reaction temperature varies depending on the starting compound, the reagent and the solvent, however, it is usually from –40° C. to the reflux temperature in the reaction system and preferably from 0° C. to 100° C.

The reaction time varies depending on the starting compound, the reagent, the solvent, the reaction temperature and the like, however, it is usually from 6 minutes to 48 hours and preferably from 10 minutes to 24 hours.

Compound (X) used in this step is a commercially available carboxylic acid or can be produced by a method for converting the carboxylic acid into an acid halide by a conventional method or a method described later.

Amine compound (IIIa) used in this step is a commercially available product or can be prepared by a known method. For example, a 5-aminoisoxazole derivative can be prepared according to a known method, for example, a method described in Bull. Chem. Soc. Jpn. 41:267 (1968), Chem. Pharm. Bull. 14:1277–1286 (1966), Heterocycles 32:1153–1158 (1991), J. Chem. Soc. Perkin Trans I 1079–1083 (1984), or J. Heterocycl. Chem. 23:1535–1538 (1986). A 4-amino-[1,2,4]oxadizole derivative can be prepared according to a known method, for example, a method described in J. Org. Chem. 28:1816–1821 (1963), J. Prakt. Chem. 313:1065–1069 (1971), U.S. Pat. No. 3,917,632 or J. Takeda Res. Lab. 30:475–492 (1971).

(Step A-2)

Step A-2 is a step of reacting compound (Ia) produced by Step A-1 with a compound represented by general formula (XI) in an inactive solvent in the presence of a base to produce compound (Ib) of the present invention.

The amount of compound (XI) used in this step is usually from 1.0 to 20.0 mol and preferably from 1.0 to 10.0 mol, based on 1 mol of compound (Ia).

The base used in this step is not particularly limited as long as it is a base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; metal hydride such as sodium hydride and potassium hydride; alkoxides such as sodium methoxide, sodium ethoxide and potassium tert-butoxide; or organic bases such as triethylamine, N,N-dimethylaniline and pyridine; is preferably alkali metal carbonate, alkali metal bicarbonate, alkali metal hydride or organic bases; and more preferably sodium carbonate, potassium carbonate, sodium hydrogen carbonate, potassium hydrogen carbonate or sodium hydride.

The amount of the base used is usually from 1.0 to 20.0 mol and preferably from 1.0 to 10.0 mol based on 1 mol of compound (Ia).

The solvent used is not particularly limited as long as it does not inhibit the reaction and dissolves the starting material to some extent. The solvent may include, for example, ethers such as diethyl ether, dimethoxyethane, tetrahydrofuran, and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably ethers, halogenated hydrocarbons, esters, aliphatic hydrocarbons or aromatic hydrocarbons, and more preferably tetrahydrofuran, ethyl acetate or toluene. Further, in this step, two-phase reaction may be carried out using the nonaqueous solvent and water.

The amount of the solvent used is usually from 1.0 to 20 liter and preferably from 1.0 to 10 liter based on 1 mol of compound (Ia).

The reaction temperature varies depending on the starting compound, the reagent and the solvent, however, it is usually from −40° C. to the reflux temperature in the reaction system and preferably from 0° C. to 100° C.

The reaction time varies depending on the starting compound, the reagent, the solvent and the reaction temperature, however, it is usually from 6 minutes to 48 hours and preferably from 10 minutes to 24 hours.

(Step B)

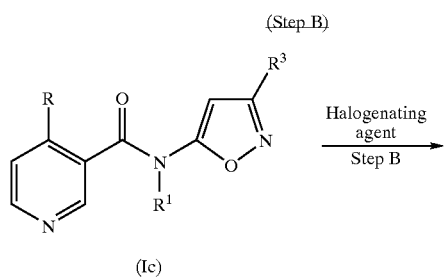

(Ic)

Halogenating agent
Step B

-continued

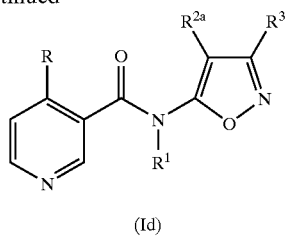

(Id)

In the formula, R, $R^1$ and $R^3$ represent the same meanings as defined above, and $R^{2a}$ represents a halogen atom.

Step B is a step of reacting a 5-isoxazolyl-4-(haloalkyl) nicotinamide derivative represented by general formula (Ic) in a case where among compound (I), X is a CH group, with a halogenating agent in an inactive solvent to produce a 5-(4-haloisoxazolyl)-4-(haloalkyl)nicotinamide derivative (Id).

The halogenating agent used in this step is not particularly limited as long as it is a compound used in a usual halogenating reaction. The halogenating agent may include, for example, molecular halogens such as chlorine, bromine and iodine; sulfonyl chlorides such as sulfuryl chloride; halogenating agents having a halogen on a nitrogen atom, such as N-chlorosuccinimide, N-bromosuccinimide, trichlorocyanuric acid and 1,3-dichloro-5,5-dimethyl hydantoin; or oxidized form of chlorine atoms, such as sodium chlorite, sodium hypochlorite or tert-butyl hypochlorite, and is preferably chlorine, bromine, sodium hypochlorite, sulfuryl chloride or N-chlorosuccinimide.

The amount of the halogenating agent used in this step is usually from 1.0 to 10.0 mol, preferably from 1.0 to 5.0 mol, based on 1 mol of compound (Ic).

The solvent used is not particularly limited as long as it does not inhibit the reaction and dissolves the starting material to some extent. The solvent may include, for example, ethers such as diethyl ether, dimethoxyethane, tetrahydrofuran, and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably esters or halogenated hydrocarbons, and more preferably dichloroethane or ethyl acetate.

The amount of the solvent used is usually from 1.0 to 20 liter and preferably from 1.0 to 10 liter, based on 1 mol of compound (Ic).

The reaction temperature varies depending on the starting compound, the reagent and the solvent, however, it is usually from −40° C. to 150° C. and preferably from 0° C. to 100° C.

The reaction time varies depending on the starting compound, the reagent, the solvent and the reaction temperature, however, it is usually from 6 minutes to 48 hours and preferably from 10 minutes to 24 hours.

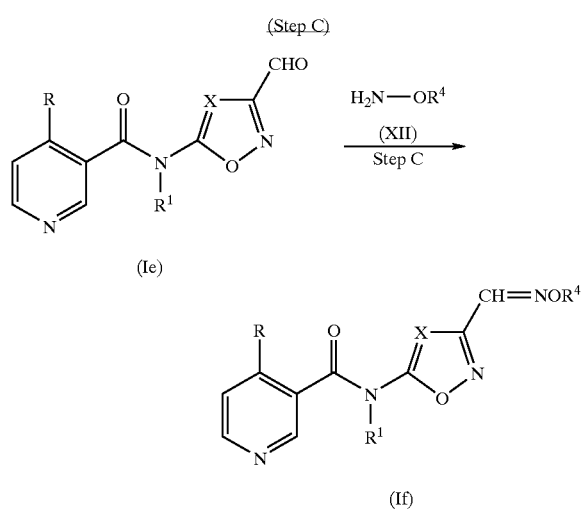

In the formula, R, $R^1$, X and $R^4$ represent the same meanings as defined above.

Step C is a step of reacting a 5-isoxazolyl-4-(haloalkyl) nicotinamide derivative represented by general formula (Ie) in a case where among compound (I), $R^3$ is a formyl group, with a hydroxylamine compound represented by formula (XII), a hydrate or salt thereof to produce an oxime compound represented by general formula (If) of the present invention.

The amount of compound (XII) used in this step is usually from 1.0 to 20.0 mol and preferably from 1.0 to 10.0 mol, based on compound (Ie).

This step may be carried out in the presence or absence of a solvent.

The solvent used is not particularly limited as long as it does not inhibit the reaction and dissolves the starting material to some extent. The solvent may include, for example, alcohols such as methanol, ethanol and ethylene glycol; ethers such as diethyl ether, dimethoxyethane, tetrahydrofuran, and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane and cyclohexane; pyridines such as pyridine and picoline; carboxylic acids such as acetic acid; water; or mixed solvents thereof, is preferably alcohols or ethers and more preferably methanol or ethanol.

The amount of the solvent used is usually from 0.1 to 20.0 liter and preferably from 1 to 10.0 liter, based on 1 mol of compound (Ie).

This step may be carried out in the presence or absence of an acid.

The acid used is not particularly limited as long as it is an acid usually exhibiting pH 6 or less. The acid may include, for example, mineral acids such as hydrochloric acid, sulfuric acid, perchloric acid and nitric acid; carboxylic acids such as formic acid, acetic acid and propionic acid; sulfonic acids such as methanesulfonic acid and benzenesulfonic acid; and an acid adduct of amines such as p-toluenesulfonate of pyridine, and is preferably carboxylic acids or sulfonic acids.

The amount of the acid used is usually from 0.01 to 100 mol and preferably from 0.01 to 30 mol, based on 1 mol of compound (Ie).

The reaction temperature varies depending on the starting compound, the reagent and the solvent, however, it is usually from −10° C. to the reflux temperature in the reaction system and preferably from room temperature to the reflux temperature in the reaction system.

The reaction time varies depending on the reaction temperature, the starting compound and the reagent, however, it is usually from 30 minutes to 48 hours and preferably from 1 hour to 24 hours.

After completion of the reaction step, the desired compounds of each step can be obtained from the reaction mixture according to a conventional method. For example, the compound is obtained by appropriately neutralizing the reaction mixture, or removing insoluble materials by filtration in the case where insoluble materials are present, adding a water-immiscible organic solvent to the reaction mixture, washing with water, and then distilling off the solvent. The desired compound obtained may, if necessary, be purified by a conventional method, such as recrystallization, reprecipitation or chromatography. Further, the desired compounds of each step may be used in the next reaction without purification.

When the N-heteroaryl-4-(haloalkyl)nicotinamide derivative of the present invention is used as an acid component of a salt, the salt can be produced, for example, by mixing the N-heteroaryl-4-(haloalkyl)nicotinamide derivative and a base in the presence or absence of a solvent and then removing the solvent.

The base used is not particularly limited as long as it is a base usually exhibiting pH 8 or more. The base may include, for example, alkali metal hydroxides such as sodium hydroxide and potassium hydroxide; alkali metal carbonates such as sodium carbonate, potassium carbonate and cesium carbonate; metal alkoxides such as sodium methoxide, sodium ethoxide and potassium tert-butoxide; alkali metal salts of organic acids, such as sodium acetate, potassium acetate, sodium formate and potassium formate; alkali metal hydrides such as sodium hydride and potassium hydride; alkali metal such as sodium and potassium; aliphatic tertiary amines such as triethylamine, tributylamine and diisopropylethylamine; alicyclic tertiary amines such as 1,4-diazobicyclo-[2,2,2]-octane (DABCO) and 1,8-diazobicyclo-[5,4,0]undec-7-ene (DBU); pyridines such as pyridine, collidine and 4-(N,N-dimethylamino)pyridine; metal amides such as lithium amide and sodium amide; or organometallics such as butyllithium, s-butyllithium, lithium diisopropylamide, sodium bis(trimethylsilyl)amide and lithium bis(trimethylsilyl)amide.

The solvent used is not particularly limited as long as it does not inhibit the reaction and dissolves the starting material to some extent. The solvent may include, for example, water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; or mixed solvents thereof.

When the N-heteroaryl-4-(haloalkyl)nicotinamide derivative of the present invention is used as a basic component of a salt, the salt can be produced, for example, by mixing the N-heteroaryl-4-(haloalkyl)nicotinamide derivative and an acid in the presence or absence of a solvent and then removing the solvent.

The acid used is not particularly limited as long as it is an acid usually exhibiting pH 6 or less. The acid may include, for example, inorganic mineral acids such as hydrochloric acid, hydrobromic acid, sulfuric acid, nitric acid and phosphoric acid; or organic acids such as formic acid, acetic acid, toluenesulfonic acid, oxalic acid and benzoic acid.

The solvent used is not particularly limited as long as it does not inhibit the reaction and dissolves the starting material to some extent. The solvent may include, for example, water; alcohols such as methanol, ethanol and t-butanol; ketones such as acetone and methyl isobutyl ketone; nitriles such as acetonitrile; esters such as ethyl acetate; halogenated hydrocarbons such as methylene chloride, chloroform and dichloroethane; ethers such as diethyl ether, tetrahydrofuran and dioxane; aromatic hydrocarbons such as toluene; amides such as dimethylformamide and dimethylacetamide; sulfoxides such as dimethyl sulfoxide; or mixed solvents thereof.

In addition, compound (X) as the starting material in Step A described above can be produced by Steps D to H described below.

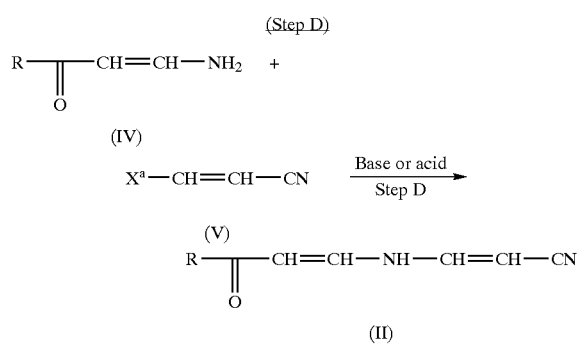

(Step D)

In the formula, R and $X^a$ represent the same meanings as defined above.

This is a step of reacting compound (V) with compound (IV) in the presence of a base or an acid in an inactive solvent or under a solvent-free condition to produce compound (II).

The amount of compound (V) used in this step is usually from 1.0 to 10.0 mol and preferably from 1.0 to 5 mol, based on 1 mol of compound (IV).

In the case of using a base in this step, the base used is not particularly limited as long as it is a base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; alkali metals such as sodium and potassium; metal hydride such as sodium hydride and potassium hydride; alkoxides such as sodium methoxide, sodium ethoxide and potassium tert-butoxide; organic bases such as triethylamine, N,N-dimethylaniline and pyridine; or organometallics such as methyllithium, butyllithium, methylmagnesium bromide and lithium diisopropylamide; is preferably alkali metal hydroxides; metal hydrides or alkoxides and more preferably sodium hydride or sodium methoxide.

The amount of the base used is usually from 1.0 to 10.0 mol and preferably from 1.0 to 5.0 mol, based on 1 mol of compound (IV).

In the case of using an acid in this step, the acid used is not particularly limited as long as it is an acid usually used in an organic chemical reaction. The acid may include, for example, mineral acids such as hydrochloric acid, sulfuric acid, perchloric acid and nitric acid; carboxylic acids such as formic acid, acetic acid and trifluoroacetic acid; sulfonic acids such as methanesulfonic acid, benzenesulfonic acid, p-toluenesulfonic acid and trifluoromethanesulfonic acid; amine salts such as pyridinium p-toluenesulfonate salt; phosphoric acids such as phosphoric acid and polyphosphoric acid; and Lewis acids such as aluminum chloride, titanium tetrachloride and boron trifluoride etherate, and is preferably mineral acids or sulfonic acids.

The amount of the acid used is usually from 1.0 to 10.0 mol and preferably from 1.0 to 5.0 mol, based on 1 mol of compound (IV).

In the case of using a solvent in this step, the solvent used is not particularly limited as long as it does not inhibit the reaction and dissolves the starting material to some extent. The solvent may include, for example, alcohols such as methanol, ethanol, propanol and t-butanol; ethers such as diethyl ether, dimethoxyethane, tetrahydrofuran, diethoxymethane and dioxane; aromatic hydrocarbons such as benzene, toluene, xylene and chlorobenzene; nitrites such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably ethers, aromatic hydrocarbons or amides and more preferably dimethoxy ethane, toluene, N,N-dimethylformamide, N,N-dimethylacetamide or 1,3-dimethyl-2-imidazolidinone.

The amount of the solvent used is usually from 1.0 to 20 liter and preferably from 1.0 to 10 liter, based on 1 mol of compound (IV).

The reaction temperature varies depending on the starting compound, the reagent and the solvent, however, it is usually from −40° C. to 150° C. and preferably from 0° C. to 100° C.

The reaction time varies depending on the starting compound, the reagent, the solvent and the reaction temperature, however, it is usually from 6 minutes to 48 hours and preferably from 10 minutes to 24 hours.

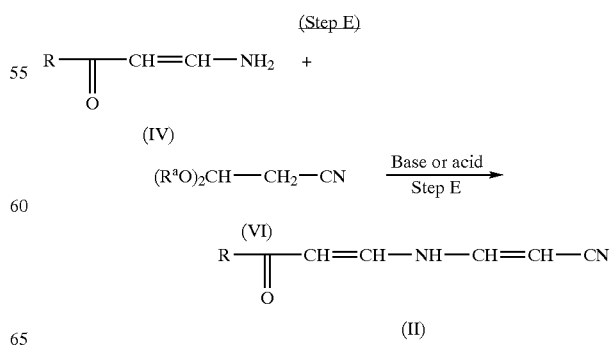

(Step E)

In the formula, R and $R^a$ represent the same meanings as defined above.

This step is a step of reacting compound (VI) with compound (IV) in the presence of a base or an acid in an inactive solvent or under a solvent-free condition to produce compound (II).

The amount of compound (VI) used in this step is usually from 1.0 to 10.0 mol and preferably from 1.0 to 5.0 mol, based on 1 mol of compound (IV).

In the case of using a base in this step, the base used is not particularly limited as long as it is the base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; metal hydride such as sodium hydride and potassium hydride; alkoxides such as sodium methoxide, sodium ethoxide and potassium tert-butoxide; organic bases such as triethylamine, N,N-dimethylaniline and pyridine; or organometallics such as methyllithium, butyllithium, methylmagnesium bromide and lithium diisopropylamide, is preferably alkali metal hydroxides, metal hydrides or alkoxides and more preferably sodium hydride or sodium methoxide.

The amount of the base used is usually from 1.0 to 10.0 mol and preferably from 1.0 to 5.0 mol, based on 1 mol of compound (IV).

In the case of using an acid in this step, the acid used is not particularly limited as long as it is an acid usually used in organic chemistry. The acid may include, for example, mineral acids such as hydrochloric acid, sulfuric acid, perchloric acid and nitric acid; carboxylic acids such as formic acid, acetic acid and trifluoroacetic acid; sulfonic acids such as methanesulfonic acid, benzenesulfonic acid, p-toluenesulfonic acid and trifluoromethanesulfonic acid; amine salts such as pyridine p-toluenesulfonate salt; phosphates such as phosphoric acid and polyphosphoric acid; and Lewis acids such as aluminum chloride, titanium tetrachloride and boron trifluoride etherate, and is preferably mineral acids or sulfonic acids.

In the case of using a solvent in this step, the solvent used is not particularly limited as long as it does not inhibit the reaction and dissolves the starting material to some extent. The solvent may include, for example, ethers such as diethyl ether, dimethoxyethane, tetrahydrofuran, diethoxymethane and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably ethers, aromatic hydrocarbons or amides and more preferably dimethoxyethane, toluene or N,N-dimethylformamide.

The amount of the solvent used is usually from 1.0 to 20 liter and preferably from 1.0 to 10 liter, based on 1 mol of compound (IV).

The reaction temperature varies depending on the starting compound, the reagent and the solvent, however, it is usually from −40° C. to 150° C. and preferably from 0° C. to 100° C.

The reaction time varies depending on the starting compound, the reagent, the solvent and the reaction temperature, however, it is usually from 6 minutes to 48 hours and preferably from 10 minutes to 24 hours.

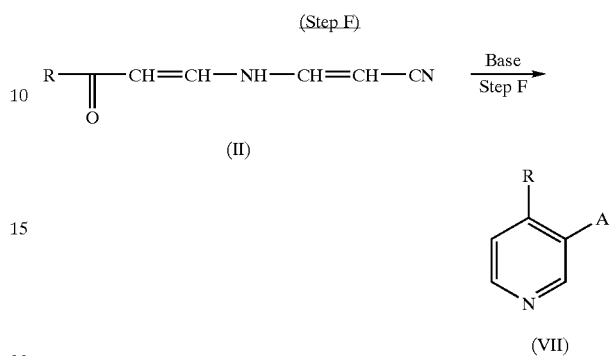

In the formula, R and A represent the same meanings as defined above.

This is a step of adding a base to compound (II) in an inactive solvent to produce compound (VII).

In this step, the base used is not particularly limited as long as it is a base usually exhibiting pH 8 or more. The base may include, for example, alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogen carbonate and potassium hydrogen carbonate; metal hydride such as sodium hydride and potassium hydride; alkoxides such as sodium methoxide, sodium ethoxide and potassium tert-butoxide; organic bases such as triethylamine, N,N-dimethylaniline and pyridine; or organometallics such as methyllithium, butyllithium, methylmagnesium bromide and lithium diisopropylamide, is preferably alkali metal hydroxides, alkali metal carbonates, alkali metal bicarbonates, metal hydrides or alkoxides and more preferably sodium hydroxide, potassium hydroxide, sodium carbonate, potassium carbonate, sodium hydride or sodium methoxide.

The amount of the base used is usually from 1.0 to 10.0 mol and preferably from 1.0 to 5.0 mol, based on 1 mol of compound (II).

The solvent used is not particularly limited as long as it does not inhibit the reaction and dissolves the starting material to some extent. The solvent may include, for example, alcohols such as methanol, ethanol, propanol and t-butanol; ethers such as diethyl ether, dimethoxyethane, tetrahydrofuran, diethoxymethane and dioxane; aromatic hydrocarbons such as benzene, toluene, xylene and chlorobenzene; nitriles such as acetonitrile; amides such as N,N-dimethylformamide, N,N-dimethylacetamide and N-methyl-2-pyrrolidone; sulfoxides such as dimethyl sulfoxide and sulfolane; halogenated hydrocarbons such as methylene chloride and chloroform; esters such as ethyl acetate and ethyl propionate; aliphatic hydrocarbons such as hexane, cyclohexane and heptane; pyridines such as pyridine and picoline; or mixed solvents thereof, is preferably alcohols, ethers, aromatic hydrocarbons or amides and more preferably methanol, ethanol, toluene or N,N-dimethylformamide.

The amount of the solvent used is usually from 1.0 to 20 liter and preferably from 1.0 to 10 liter, based on 1 mol of compound (II).

The reaction temperature varies depending on the starting compound, the reagent and the solvent, however, it is usually from −40° C. to 150° C. and preferably from 0° C. to 100° C.

The reaction time varies depending on the starting compound, the reagent, the solvent and the reaction temperature, however, it is usually from 6 minutes to 48 hours and preferably from 10 minutes to 24 hours.

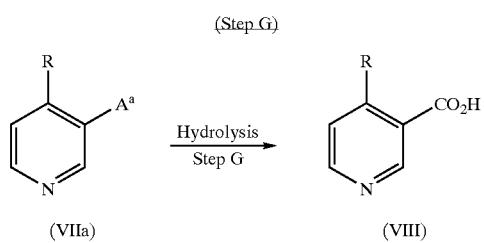

(VIIa)    (VIII)

In the formula, R represents the same meaning as defined above, and $A^a$ represents a cyano group or a carbamoyl group.

This is a step of hydrolyzing compound (VIIa) in which among compound (VII), A is a cyano group or a carbamoyl group, by adding an acid or alkali in a solvent to produce compound (VIII), and may be carried out in a usual hydrolysis condition.

In this step, the acid used is not particularly limited as long as it is an acid used in usual hydrolysis. The acid may include, for example, inorganic acids such as hydrochloric acid and sulfuric acid. It is preferably hydrochloric acid or sulfuric acid.

The amount of the acid used is usually from 1 equivalent to a large excessive amount based on compound (VIIa).

In this step, the alkali used is not particularly limited as long as it is an alkali used in usual hydrolysis. The alkali may include, for example, alkali metal hydroxides such as sodium hydroxide and potassium hydroxide. It is preferably sodium hydroxide or potassium hydroxide.

The amount of the alkali used is usually from 1 to 20 equivalents based on compound (VIIa).

The solvent used is not particularly limited as long as it is a solvent used in usual hydrolysis. The solvent may include, for example, water; alcohols such as methanol, ethanol, propanol and t-butanol; ethers such as diethyl ether, dimethoxyethane, tetrahydrofuran, diethoxymethane and dioxane; or mixed solvents thereof. It is preferably water.

The reaction temperature varies depending on the starting compound, the reagent and the solvent, however, it is usually from 0° C. to the reflux temperature.

The reaction time varies depending on the starting compound, the reagent, the solvent and the reaction temperature, however, it is usually from 5 minutes to 48 hours.

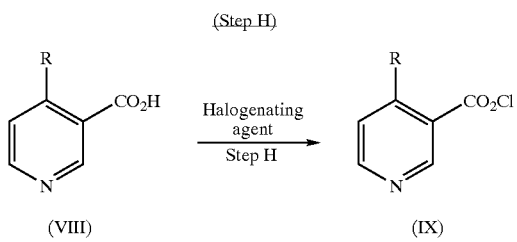

(VIII)    (IX)

In the formula, R represents the same meaning as defined above.

This step is a method for reacting compound (VIII) in which among compound (VII), A is a carboxylic group, with a halogenating agent in an inactive solvent to produce compound (IX).

The halogenating agent used in this step is not particularly limited as long as it is an agent usually used in dehydrative halogenation. The halogenating agent may include, for example, sulfur halides such as thionyl chloride and sulfuryl chloride; phosphorus halides such as phosphorus pentachloride; or organic halides such as phosgene, diphosgene, triphosgene and oxalyl chloride. It is preferably sulfur halides or organic halides and more preferably thionyl chloride or sulfuryl chloride.

The solvent used is not particularly limited as long as it does not inhibit the reaction and dissolves the starting material to some extent. The solvent may include, for example, ethers such as dimethyl ether, t-butyl methyl ether, dimethoxyethane, tetrahydrofuran and dioxane; aromatic hydrocarbons such as benzene, toluene, xylene and chlorobenzene; nitriles such as acetonitrile; amides such as N,N-dimethylamide, N,N-dimethylacetamide and N-methyl-2-pyrrolidone; halogenated hydrocarbons such as methylene chloride and dichloroethane; esters such as ethyl acetate and propyl acetate; aliphatic hydrocarbons such as hexane, cyclohexane and heptane; pyridines such as pyridine and picoline; or mixed solvents thereof, is preferably ethers, aromatic hydrocarbons or halogenated hydrocarbons and more preferably toluene, xylene and dicloroethane.

The amount of the halogenating agent used in this step is usually from 1.0 to 10.0 mol and preferably from 1.0 to 5.0 mol, based on 1 mol of compound (VIII).

The amount of the solvent used is usually from 0.1 to 20.0 liter and preferably from 0.5 to 10 liter, based on 1 mol of compound (VIII).

The reaction temperature varies depending on the starting compound, the reagent and the solvent, however, it is usually from −40° C. to 150° C. and preferably from 0° C. to the reflux temperature of the solvent.

The reaction time varies depending on the starting compound, the reagent, the solvent and the reaction temperature, however, it is usually from 6 minutes to 48 hours and preferably from 10 minutes to 24 hours.

After completion of each reaction step above, the desired compounds of each step can be obtained from the reaction mixture according to a conventional method. For example, the compounds are obtained by appropriately neutralizing the reaction mixture, or removing insoluble materials by filtration in the case where insoluble materials are present, adding a water-immiscible organic solvent to the reaction mixture, washing with water, and then distilling off the solvent. The desired compound obtained may, if necessary, be further purified by a conventional method, such as recrystallization, reprecipitation or chromatography. In addition, the desired compounds of each step may be used in the next reaction without purification.

When the compound of the present invention is used as an active component of pesticides, it may be used by itself. However, it can be formulated into various formulations such as an emulsifiable concentrate, a suspension, a dust, a granule, a tablet, a wettable powder, a water-soluble powder, a liquid formulation, a flowable concentate, a water dispersible granule, an aerosol, a paste, an oil-based formulation and a concentrated emulsion in water in combination with carriers, surfactants and other adjuvants which are commonly used for formulation as agricultural adjuvants. They are blended usually in such proportions that the active component is from 0.1 to 9.0 parts by mass and the agricultural adjuvant is from 10 to 99.9 parts by mass.

The carrier used for the above formulation may be classified into a solid carrier and a liquid carrier. The solid carrier may include, for example, animal and plant powders such as starch, activated charcoal, soybean powder, wheat flour, wood flour, fish flour and powdered milk; and mineral powders such as talc, kaolin, bentonite, calcium carbonate, zeolite, diatomaceous earth, white carbon, clay and alumina. The liquid carrier may include, for example, water; alcohols such as isopropyl alcohol and ethylene glycol; ketones such as cyclohexane and methyl ethyl ketone; ethers such as dioxane and tetrahydrofuran; aliphatic hydrocarbons such as kerosene and light oil; aromatic hydrocarbons such as xylene, trimethylbenzene, tetramethylbenzene, methylnaphthalene and solvent naphtha; halogenated hydrocarbons such as chlorobenzene; acid amides such as dimethylacetamide; esters such as glycerin esters of fatty acids; nitriles such as acetonitrile; and sulfur-containing compounds such as dimethyl sulfoxide. The carrier used is preferably a solid carrier or a liquid carrier.

The surfactants used may include, for example, metal salts of alkylbenzenesulfonic acids, metal salts of dinaphthylmethane disulfonic acids, salts of alcohol sulfates, alkylarylsulfonates, lignin sulfonates, polyoxyethylene glycol ethers, polyoxyethylene alkyl aryl ethers or polyoxyethylene sorbitan monoalkylates, and are preferably metal salts of alkylbenzenesulfonic acids, lignin sulfonates, polyoxyethylene alkyl aryl ethers or polyoxyethylene sorbitan monoalkylates.

The other adjuvants may include, for example, sticking agents and thickeners such as carboxydimethylcellulose, gum arabic, sodium arginate, xanthan gum, guar gum, tragacanth gum and polyvinyl alcohol; antifoaming agents such as metal soap; or physical property improvers or coloring agents such as fatty acids, alkyl phosphates, silicone and paraffin, and are preferably guar gum or xanthan gum.

When these formulations are practically used, they may be used directly or after diluted with a diluent such as water to a predetermined concentration. Various formulations containing the compounds of the present invention, whether diluted or not, may be applied by conventional methods, i.e., application methods (such as spraying, misting, atomizing, dusting, granule application, submerged application and seeding box application), soil treatment (such as mixing or drenching), surface application (such as painting, dressing and covering), dipping or poison bait. Further, the above active components may be incorporated into livestock feeds for feeding so as to prevent pest insects after they are voided in excrement, especially, infestation or growth of pest insects. Otherwise, they can also be applied by a so-called application method in low volume at ultra high concentration. In this method, the active component may be contained up to 100%.

The pesticides of the present invention are applied usually at an active component concentration of from 0.1 to 50000 ppm and preferably from 1 to 10000 ppm. However, the active component concentration can be suitably changed in accordance with the type of formulation, and the method, the purpose, the season or the site of application, and the infestation degree of the pest. For example, in a case of an aquatic pest, the pest can be controlled also when applying a formulation within the above-described concentration range to the infested site and therefore, the concentration of the active component in water may be below the above-described range. In a case of soil admixture treatment, the dose of pesticides of the present invention is, for example, from 0.1 to 5000 g and preferably from 1 to 1000 g, per 10 ares in terms of the compound that serves as the active component.

Needless to say, the compounds of the present invention are sufficiently effective when used alone. However, they may be used, if necessary, in combination or in admixture with fertilizers or other agrochemicals such as insecticides, miticides, nematicides, fungicides, antivirus agents, attractants, herbicides and plant growth regulants, and such combined use can sometimes produce improved effects.

Other agrochemicals which may be used in admixture with the compounds of the present invention may include, for example, insecticides, miticides, nematicides, fungicides, antivirus agents, attractants, herbicides and plant growth regulants, and are preferably insecticides, miticides, nematicides, fungicides or herbicides.

The insecticides used may include, for example, organophosphorus compounds and carbamate insecticides, pyrethroid insecticides or other insecticides.

The organophosphorus compounds and carbamate insecticides may include, for example, fenthion, fenitrothion, diazinon, chlorpyriphos, oxydeprofos, vamidothion, phenthoate (fentoat), dimethoate, formothion, malathion, trichlorphon, thiometon, phosmet, dichlorvos, acephate, EPBP, methyl-parathion, oxydimeton-methyl, ethion, dioxabenzofos, cyanophos (cyanofos), isoxathion, pyridafenthion, phosalone, metidation, sulprophos (sulprofos), chlorfenvinphos, tetrachlorvinphos, dimethylvinphos, propahos, isofenphos, disulfoton, profenofos, pyraclofos, monocrotophos, azinphos-methyl, aldikarb, methomyl, thiodicarb, carbofuran, carbosulfan, benfuracarb, furathiocarb, propoxur, fenobcarb, metolcarb, isoprocarb, carbaryl (carbaril), pirimicarb, ethiofencarb, dichlophenthion, pirimiphos-methyl, quinalphos, chlorpyriphos-methyl, prothiophos, naled, EPN, XMC, bendiocarb, oxamyl, alanycarb or chlorethoxyfos.

The pyrethroid insecticides may include, for example, permethrin, cypermethrin, deltamethrin, fenvalerate, fenpropathrin, piretrine, allethrin, tetramethrin, resmethrin, dimethrin, proparthrin, phenothrin, prothrin, fluvalinate, cyfluthrin, cyhalothrin, flucythrinate, etofenprox, cyclopro thrin, tralomethrin, silafluofen, tefluthrin, bifenthrin or acrinathrin.

Other insecticides may include, for example, diflubenzuron, chlorfluazuron, hexaflumuron, triflumuron, teflubenzuron, flufenoksuron, flucycloxuron, buprofezin, pyriproxyfen, lufenuron, cyromazine, methoprene, endosulphan, diafenthiuron, imidacloprid, fipronil, fenoxycarb, cartap, thiocyclam, bensultap, tebufenozide, chlorphenapyr, emamectin-benzoate, acetaprid, nitenpyram, pymetrozine, sodium oleate, nicotin-sulfate, rotenone, metaldehyde, machine oil, rapeseed oil and microbial pesticides such as BT or insect viruses.

The miticides used may include, for example, chlorobenzilate, phenisobromolate, dicofol, amitraz, propargit, benzomate, hexythiazox, fenbutatin oxide, polynactin, quinomethionate, chlorfenson, tetradifon, avermectin, milbemectin, clofentezine, pyridaben, fenpyroximate, tebufenpyrad, pyrimidifen, fenothiocarb, dienochlor, etoxazole or halfenprox.

The nematicides used may include, for example, phenamiphos, fosthiazate, ethoprophos, methyl isothiocyanate, 1,3-dichloropropene or DCIP.

The fungicides used may include, for example, thiophanate-methyl, benomyl, carbendazole, thiabendazole, folpet, Thiuram, ziram, zineb, maneb, mancozeb, polycarbamate, iprobenfos (IBP), edifenphos, fusaride, probenazole, isoprothiolane, chlorothalonil, captan, polyoxin, blasticidin-S, kasugamycin, streptomycin, validamycin, tricyclazole, pyroquilon, fenadineoxide, mepronil, flutolanil, pencycuron, iprodione, hymexazole, metalaxyl, triflumizole, triforine, triadimefon, bitertanol, fenarimol, propiconazole, cymoxanil, prochloraz, pefurazoate, hexaconazole, myclobutanil, diclomezine, tecloftalam, propineb, dithianon, fosetyl, vinclozolin, procymidone, oxadixyl, guazatine, propamocarb, fluazinam, oxolinic acid, hydroxyisoxazole, imibenconazole or mepanipyrim.

The herbicides used may include, for example, diflufenican, propanil, dichloropicolinic acid, dicamba, picloram, 2,4-D, 2,4-DB, 2,4-DP, fluroxypyr, MCPA, MCPP, triclopyr, diclofop-methyl, fenoxaprop-ethyl, fluazifop-butyl, haloxyfop-methyl, quizalofop-ethyl, norflurazon, chlorpropham, desmedipham, phenmedipham, propham, alachlor, acetochlor, butachlor, metazachlor, metolachlor, pretilachlor, propachlor, oryzalin, trifluralin, acifluorfen, bifenox, fluoroglycofen, fomesafen, halosafen, lactofen, oxyfluorfen, chlortoluron, diuron, fluometuron, isoproturon, linuron, methabenzthiazuron, alloxydim, clethodim, cycloxydim, sethoxydim, tralkoxydim, imazethapyr, imazamethabenz, imazapyr, imazaquin, bromoxynil, dichlobenil, ioxynil, mefenacet, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron, tribenuron-methyl, butylate, cycloate, di-allate, EPTC, esprocarb, molinate, prosulfocarb, thiobencarb, tri-allate, atrazine, cyanazine, simazine, simetryn, terbutryn, terbutylazine, hexazinone, metamitron, metribuzin, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate or tridiphane.

The compounds of the present invention exhibit excellent pesticidal activities, for example, against hemipteran pest, lepidopteran pest, coleopteran pest, dipteran pest, hymenopteran pest, orthopteran pest, isopteran pest, thysanopteran pest, mites and plant-parasitic nematodes pest. Further, the compounds of the present invention exhibit excellent pesticidal activities also against other pests, unfavorable animals, sanitary pests and parasites.

The hemipteran pest may include, for example, bugs (*Heteroptera*) such as bean bug (*Riptortus clavatus*), southern green stink bug (*Nezara viridula*), *lygus* bugs (*Lygus* sp.), hairy chinch bug (*Blissus leucopterus*) and pear lace bug (*Stephanitis nashi*); leafhoppers (*Circulifer* sp.) such as green rice leafhopper (*Nephotettix cincticeps*) and leafhoppers (*Empoasca* sp., *Erythroneura* sp., *Circulifer* sp.); delphacid planthoppers such as brown rice planthopper (*Nilaparvata lugens*), white-backed planthopper (*Sogatella furcifera*) and small brown planthopper (*Laodelphax striatellus*); jumping plantlice such as Psyllids (*Psylla* sp.); whiteflies such as sweetpotato whitefly (*Bemisia tabaci*) and greenhouse whitefly (*Trialeurodes vaporariorum*); aphids such as grapeleaf louse (*Viteus vitifolii*), green peach aphid (*Myzus persicae*), green apple aphid (*Aphis pomi*), cotton aphid (*Aphis gossypii*), *Aphis fabae, Liphis erysimi*, glasshouse-potato aphid (*Aulacorthum solani*) and greenbug (*Schizaphis graminum*); mealy bugs or scales such as Comstock mealybug (*Pseudococcus comstocki*), red wax scale (*Ceroplastes rubens*), San Jose scale (*Comstockaspis perniciosa*) and arrowhead scale (*Unaspis yanonensis*) and *Rhodimius* sp.

The lepidopteran pest may include, for example, tortricids such as oriental tea tortrix (*Homona magnanima*), summer fruit tortrix (*Adoxophyes orana*), tortricids (*Sparganothis pilleriana*), oriental fruit moth (*Grapholitha molesta*), soybean pod borer (*Leguminivora glycinivorella*), codling moth (*Laspeyresia pomonella*), *Eucosma* sp. and *Lobesia botrana*; Cochylidae such as grape cochylid (*Eupoecillia ambiguella*); bagworm moths such as *Bambalina* sp.; tineids such as European grain moth (*Nemapogon granellus*) and casemaking clothes moth (*Tinea translucens*); lyonetiid moths such as *Lyonetia prunifoliella*; leafblotch miners such as apple leafminer (*Phyllonorycter rigoniella*); Phyllocnistidae such as citrus leafminer (*Phyllocnistis citrella*); yponomeutids such as diamondback moth (*Plutella xylostella*) and Prays citri; clearwing moths such as grape clearwing moth (*Paranthrene regalis*) and *Synanthedon* sp.; gelechiid moths such as pink bollworm (*Pectinophora gossypiella*), potato tuberworm (*Phthorimaea operculella*) and *Stomopteryx* sp.; Carposimidae such as peach fruit moth (*Carposina niponensis*); slug caterpillarmoths such as oriental moth (*Monema flavescens*); pyralid moths such as Asiatic rice borer (*Chilo suppressalis*), rice leafroller (*Cnaphalocrocis medinalis*), *Ostrinia nubilalis*, oriental corn borer (*Ostrinia furnacalis*), cabbage webworm (*Hellula undalis*), greater wax moth (*Galleria mellonella*), *Elasmopalpus lignosellus* and *Loxostege sticticalis*; whites such as common cabbageworm (*Pieris rapae*); geometrid moths such as mugwort looper (*Ascotis selenaria*); tent caterpillar moths such as tent caterpillar (*Malacosoma neustria*); sphinx moths such as *Manduca sexta*; tussock moths such as tea tussock moth (*Euproctis pseudoconspersa*) and gypsy moth (*Lymantria dispar*); tiger moths such as fall webworm (*Hyphantria cunea*); and owlet moths such as tobacco budworm (*Heliothis virescens*), bollworm (*Helicoverpa zea*), beet armyworm (*Spodoptera exigua*), cotton bollworm (*Helicoverpa armigera*), common cutworm (*Spodoptera litura*), cabbage armyworm (*Mamestra brassicae*), black cutworm (*Agrotis ipsiron*), rice armyworm (*Pseudaletia separata*) and cabbage looper (*Trichoplusia ni*).

The coleopterann pest may include, for example, chafers such as cupreous chafer (*Anomala cuprea*), Japanese beetle (*Popillia japonica*), soybean beetle (*Anomala rufocuprea*) and Eutheolarugiceps; click beetles such as wireworm (*Agriotes* sp.) and *Conodeus* sp.; ladybirds such as twenty-eight-spotted ladybird (*Epilachna vigintioctopunctata*) and Mexican bean beetle (*Epilachna varivestis*); darkling beetles such as red flour beetle (*Tribolium castaneum*); longicorn beetles such as white-spotted longicorn beetle (*Anoplophora malasiaca*) and pine sawyer (*Monochamus alternatus*); seed beetles such as bean weevil (*Acanthoscelides obtectus*) and adzuki bean weevil (*Callosobruchus chinensis*); leaf beetles such as colorado potato beetle (*Leptinotarsa decemlineata*), corn rootworm (*Diabrotica* sp.), rice leaf beetle (*Oulema* oryzae), beet flea beetle (*Chaetocnema concinna*), *Phaedon cochleariais*, *Oulema melanopus* and *Dicladispa armigera*; Apionidae such as *Apion godmani*; weevils such as rice water weevil (*Lissorhoptrus oryzophilus*) and cotton boll weevil (*Anthonomus grandis*); Rhynchophoridae such as maize weevil (*Sitophilus zeamais*); bark beetles; dermestid beetles; and drugstore beetles.

The dipteran pest may include, for example, rice crane fly (*Tipula aino*), rice midge (*Chironomus oryzae*), *Orseolia oryzae*, *Ceratitis capitata*, rice leafminer (*Hydrellia griseola*), cherry drosophila (*Drosophila suzukii*), frit fly (*Oscinella frit*), rice stem maggot (*Chlorops oryzae*), French bean miner (*Ophiomyia phaseoli*), legume leafminer (*Liriomyza trifolii*), spinach leafminer (*Pegomya hyoscyami*), seedcorn maggot (*Delia platura*), sorghum fly (*Atherigona soccata*), muscid fly (*Musca domestica*), *Gastrophilus* sp., stomoxiid flies (*Stomoxys* sp.), *Aedes aegypti*, *Culex pipiens*, *Anopheles slnensis* and *Culex tritaeniorhynchus*.

The hymenopteran pest may include, for example, stem sawflies (*Cephus* sp.); eurytomids (*Harmolita* sp.); cabbage sawflies (*Athalia rosae* sp.), hornets (*Vespa mandarins* sp.) and fire ants.

The orthopteran pest may include, for example, German cockroach (*Blatella germanica*); American cockroach (*Periplaneta americana*); African mole cricket (*Gryllotalpa africana*); Asiatic locust (*Locusta migratoria* migratoriodes); and *Melanoplus sanguinipes*.

The isopteran pest may include, for example, termites (*Reticulitermes speratus*), Formosan subterranean termite (*Coptotermes formosanus*) and termites (*Cryptotermes domestius*).

The thysanoptran pest may include, for example, yellow tea thrips (*Scirtothrips dorsalis*); thrips (*Thrips palmi*); greenhouse thrips (*Heliothrips haemorrholidalis*); western flower thrips (*Frankliniella occidentalis*) and rice aculeated thrips (*Haplothrips aculeatus*).

The mites may include, for example, two-spotted spider mite (*Tetranychus urticae*); Kanzawa spider mite (*Tetranychus kanzawai*); citrus red mite (*Panonychus citri*); European red mite (*Panonychus ulmi*), yellow spider mite (*Eotetranychus carpini*); Texas citrus mite (*Eotetranychus banksi*); citrus rust mite (*Aculops pelekassi*); broad mite (*Polyphagotarsonemus latus*); false spider mites (*Brevipalpus* sp.); bulb mite (*Rhizoglyphus robini*) and mold mite (*Tyrophagus putrescentiae*).

The plant-parasitic nematodes may include, for example, southern root-knot nematode (*Meloidogyne incognita*); root-lesion nematode (*Pratylenchus* sp.); soybean cyst nematode (*Heterodera glycines*); rice white-tip nematode (*Aphelenchoides besseyi*) and pine wood nematode (*Bursaphelenchus lignicolus*).

Other pests, unfavorable animals, sanitary pests, and parasites may include, for example, gastropods (*Gastropoda*) such as apple snails (*Pomacea canaliculata*), slugs (*Incilaria* sp.) and giant African snail (*Achatina fulica*); isopods (Isopoda) such as pillbug (*Armadillidium* sp.), sow bug and centipede; booklice such as *Liposcelis* sp.; siverfish such as *Ctenolepisma* sp.; fleas such as *Pulex* sp. and *Ctenocephalides* sp.; bird lice such as *Trichodectes* sp.; bed bugs such as *Cimex* sp.; aminal-parasitic mites such as *Boophilus microplus* and *Haemaphysalis longicornis* and Epidermoptidae.

Further, the compounds of the present invention are effective also against pests exhibiting resistance to organophosphorus compounds, carbamate compound, synthetic pyrethroid compounds, acyl urea compounds or conventional pesticides.

BEST MODE FOR CARRYING OUT THE INVENTION

The compounds of the present invention are described in detail below by referring to Examples, Reference Examples, Formulation Examples and Test Examples, however, the present invention is not limited thereto.

EXAMPLE 1

N-(3-Methyl-5-isoxazolyl)-4-(trifluoromethyl)nicotinamide (Compound No. 1-2, Step A-1)

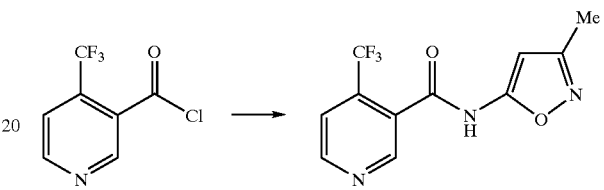

5-Amino-3-methylisoxazole (147 mg, 1.5 mmol) was dissolved in dimethylformamide (5 ml), sodium hydride (60% dispersion in mineral oil, 72 mg, 1.8 mmol) was added and subsequently, 4-trifluoromethylnicotinic acid chloride (314 mg, 1.5 mmol) was added under ice-cooling. The mixture was stirred under heating at 80° C. for 2 hours. The reaction mixture was poured into ice-water and extracted with ethyl acetate. The organic layer was washed with brine and then dried over anhydrous magnesium sulfate. The solvent was removed by distillation under reduced pressure, and the resulting residue was purified by thin layer chromatography (a developing solvent: ethyl acetate/hexane=1/1) to obtain the title compound (181 mg, yield 44%).

$^1$H-NMR (CDCl$_3$) δ (ppm): 10.35 (1H, brd.s), 8.91 (1H, s), 8.88 (1H, d, J=5.1 Hz), 7.66 (1H, d, J=5.1 Hz), 6.41 (1H, s), 2.27 (3H, s). Melting point: 53–55° C.

EXAMPLE 2

N-Ethoxymethyl-N-(3-methyl-5-isoxazolyl)-4-(trifluoromethyl)nicotinamide (Compound No. 1-51, Step A-2)

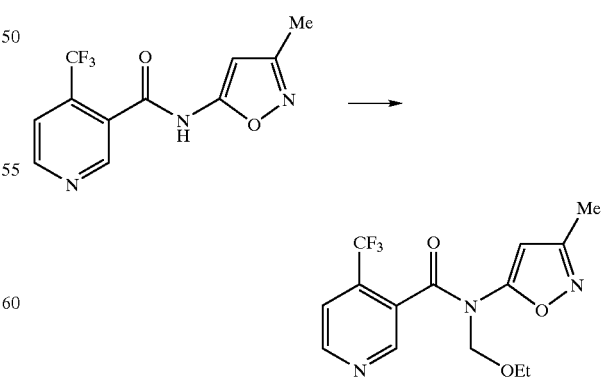

N-(3-Methyl-5-isoxazolyl)-4-(trifluoromethyl)nicotinamide (Compound No. 1-2, 107.1 mg, 0.39 mmol) prepared according to Example 1 was dissolved in dimethylformamide (2 ml). To this solution, potassium carbonate (81.4 mg, 0.59 mmol) and bromoacetonitrile (30 μl, 0.43 mmol) were added, and the mixture was stirred at room temperature for 2 hours. The reaction mixture was poured into water and extracted with ethyl acetate. The extract was washed with brine, dried over anhydrous magnesium sulfate and concentrated. The resulting residue was purified by thin layer chromatography (a developing solvent: hexane/ethyl acetate=1/1) to obtain the title compound (91.3 mg, yield 75%).

$^1$H-NMR (DMSO-$d_6$) δ (ppm): 8.93 (1H, d, J=5.1 Hz), 8.85 (1H, s), 7.90 (1H, d, J=5.1 Hz), 6.28 (1H, s), 5.22 (2H, s), 3.59 (2H, q, J=7.0 Hz), 2.12 (3H, s), 1.11 (3H, t, J=7.0 Hz). Physical property: oil.

EXAMPLE 3

N-(4-Chloro-3-methyl-5-isoxazolyl)-4-(trifluoromethyl)nicotinamide (Compound No. 1-21, Step B)

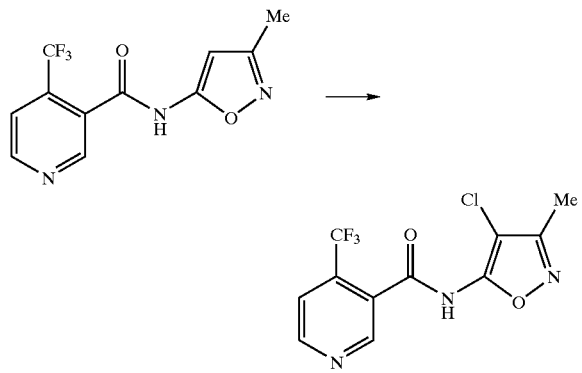

To N-(3-methyl-5isoxazolyl)-4-(trifluoromethyl)nicotinamide (Compound No. 1-2, 101.7 mg, 0.37 mmol) prepared according to Example 1, carbon tetrachloride (2 ml) and N-chlorosuccinimide (64.6 mg, 0.48 mmol) were added, and the mixture was heated under reflux for 1.5 hours. The reaction mixture was poured into water and extracted with ethyl acetate. The extract was washed with brine, dried over anhydrous magnesium sulfate and concentrated. The resulting residue was purified by thin layer chromatography (a developing solvent: hexane/ethyl acetate=1/1) to obtain the title compound (69.3 mg, yield 61%).

$^1$H-NMR (CDCl$_3$) δ (ppm): 8.94 (1H, s), 8.92 (1H, d, J=5.1 Hz), 8.41 (1H, brd.s), 7.67 (1H, d, J=5.1 Hz), 2.29 (3H, s) Melting point: 153–156° C.

Furthermore, the following compounds were prepared according to any one of Examples 1 to 3.

EXAMPLE 4

N-(5-Isoxazolyl)-4-(trifluoromethyl)nicotinamide (Compound No. 1-1)

$^1$H-NMR (CDCl$_3$) δ (ppm): 10.07 (1H, brd.s), 8.94 (1H, s), 8.91 (1H, d, J=5.1 Hz), 8.19 (1H, d, J=1.8 Hz), 7.56 (1H, d, J=5.1 Hz), 6.56 (1H, d, J=1.8 Hz). Physical property: amorphous.

EXAMPLE 5

N-(3-Ethyl-5-isoxazolyl)-4-(trifluoromethyl)nicotinamide (Compound No. 1-3)

$^1$H-NMR (CDCl$_3$) δ (ppm): 10.01 (1H, brd.s), 8.92 (1H, s), 8.90 (1H, d, J=5.1 Hz), 7.68 (1H, d, J=5.1 Hz), 6.45 (1H, s), 2.66 (2H, q, J=7.7 Hz), 1.28 (3H, t, J=7.7 Hz). Physical property: oil.

EXAMPLE 6

N-(3-Isopropyl-5-isoxazolyl)-4-(trifluoromethyl)nicotinamide (Compound No. 1-5)

$^1$H-NMR (CDCl$_3$) δ (ppm): 10.31 (1H, brd. s), 8.91 (1H, s), 8.89 (1H, d, J=5.1 Hz), 7.67 (1H, d, J=5.1 Hz), 6.46 (1H, s), 3.01 (1H, m), 1.29 (6H, d, J=7.0 Hz). Physical property: oil.

EXAMPLE 7

N-(3-Formyl-5-isoxazolyl)-4-(trifluoromethyl)nicotinamide (Compound No. 1-16)

$^1$H-NMR (CDCl$_3$) δ (ppm): 10.10 (1H, s), 8.98 (1H, d, J=5.1 Hz), 8.97 (1H, s), 7.71 (1H, d, J=5.1 Hz), 6.93 (1H, s). Physical property: amorphous.

EXAMPLE 8

N-(3-Hydroxyiminomethyl-5-isoxazolyl)-4-(trifluoromethyl)nicotinamide (Compound No. 1-17)

$^1$H-NMR (CDCl$_3$) δ (ppm): 8.97 (1H, d, J=5.1 Hz), 8.96 (1H, s), 8.08 (1H, s), 7.86 (1H, d, J=5.1 Hz), 6.72 (1H, s). Physical property: amorphous.

EXAMPLE 9

N-(3-Cyano-5-isoxazolyl)-4-(trifluoromethyl)nicotinamide (Compound No. 1-18)

$^1$H-NMR (CDCl$_3$) δ (ppm): 8.94 (1H, d, J=5.1 Hz), 8.91 (1H, s) 7.73 (1H, d, J=5.1 Hz), 6.90 (1H, s). Melting point: 135–139° C.

EXAMPLE 10

N-(3-Methoxymethyl-5-isoxazolyl)-4-(trifluoromethyl)nicotinamide (Compound No. 1-19)

$^1$H-NMR (CDCl$_3$) δ (ppm): 9.90 (1H, brd.s), 8.93 (1H, s), 8.92 (1H, d, J=5.1 Hz), 7.69 (1H, d, J=5.1 Hz), 6.60 (1H, s), 4.50 (2H, s), 3.42 (3H, s). Physical property: amorphous.

EXAMPLE 11

N-(4-Chloro-5-isoxazolyl)-4-(trifluoromethyl)nicotinamide (Compound No. 1-20)

$^1$H-NMR (CDCl$_3$) δ (ppm): 8.94 (1H, s), 8.91 (1H, d, J=5.1 Hz), 8.27 (1H, s), 7.67 (1H, d, J=5.1 Hz). Physical property: oil.

EXAMPLE 12

N-(4-Chloro-3-cyclopropyl-5-isoxazolyl)-4-(trifluoromethyl)nicotinamide (Compound No. 1-25)

$^1$H-NMR (CDCl$_3$) δ (ppm): 8.96 (1H, brd.s), 8.90–8.84 (2H, m), 7.65 (1H, d, J=5.1 Hz), 1.94–1.80 (1H, m), 1.08–1.04 (4H, m). Physical property: amorphous.

EXAMPLE 13

N-(4-Chloro-3-methoxymethyl-5-isoxazolyl)-4-(trifluoromethyl)nicotinamide (Compound No. 1-37)

$^1$H-NMR (CDCl$_3$) δ (ppm): 8.92 (1H, s), 8.91 (1H, d, J=5.1 Hz), 7.67 (1H, d, J=5.1 Hz), 4.51 (2H, s), 3.42 (3H, s). Melting point: 69–72° C.

EXAMPLE 14

N-(4-Bromo-3-methyl-5-isoxazolyl)-4-(trifluoromethyl)nicotinamide (Compound No. 1-41)

$^1$H-NMR (CDCl$_3$) δ (ppm): 8.92 (1H, s), 8.90 (1H, d, J=5.1 Hz), 7.66 (1H, d, J=5.1 Hz), 2.29 (3H, s). Melting point: 165–166° C.

EXAMPLE 15

N-(4-Iode-3-methyl-5-isoxazolyl)-4-(trifluoromethyl)nicotinamide (Compound No. 1-43)

$^1$H-NMR (CDCl$_3$) δ (ppm): 8.97 (1H, s), 8.95 (1H, d, J=5.1 Hz), 7.68 (1H, d, J=5.1 Hz), 2.30 (3H, s). Melting point: 198–201° C.

EXAMPLE 16

N-Methyl-N-(3-methyl-5-isoxazolyl)-4-(trifluoromethyl)nicotinamide (Compound No. 1-47)

$^1$H-NMR (DMSO-d$_6$) δ (ppm): 8.92 (1H, d, J=5.2 Hz), 8.85 (1H, s), 7.83 (1H, d, J=5.2 Hz), 6.06 (1H, brd.s), 3.36 (3H, s), 2.12 (3H, s). Physical property: oil.

EXAMPLE 17

N-Allyl-N-(5-isoxazolyl)-4-(trifluoromethyl)nicotinamide (Compound No. 1-48)

$^1$H-NMR (DMSO-d$_6$) δ (ppm): 8.89 (1H, d, J=5.2 Hz), 8.78 (1H, s), 7.81 (1H, d, J=5.2 Hz), 6.05 (1H, s), 5.95–5.80 (1H, m), 5.29–5.19 (2H, m), 4.44 (2H, d, J=5.8 Hz), 2.08 (3H, s). Physical property: oil.

EXAMPLE 18

N-Allyl-N-(3-methyl-5-isoxazolyl)-4-(trifluoromehyl)nicotinamide (Compound No. 1-49)

$^1$H-NMR (DMSO-d$_6$) δ (ppm): 8.89 (1H, d, J=5.2 Hz), 8.78 (1H, s), 7.81 (1H, d, J=5.2 Hz), 6.05 (1H, s), 5.95–5.80 (1H, m), 5.29–5.19 (2H, m), 4.44 (2H, d, J=5.8 Hz), 2.08 (3H, s). Physical property: oil.

EXAMPLE 19

N-Cyanomethyl-N-(3-methyl-5-isoxazolyl)-4-(trifluoromethyl)nicotinamide (Compound No. 1-53)

$^1$H-NMR (DMSO-d$_6$) δ (ppm): 8.96 (1H, d, J=5.1 Hz), 8.91 (1H, s), 7.92 (1H, d, J=5.1 Hz), 6.24 (1H, s), 5.09 (2H, s), 2.11 (3H, s). Physical property: oil.

EXAMPLE 20

N-(3-Methyl-5-isoxazolyl)-N-methylthiomethyl-4-(trifluoromethyl)nicotinamide (Compound No. 1-55)

$^1$H-NMR (CDCl$_3$) δ (ppm): 8.82 (1H, d, J=5.1 Hz), 8.63 (1H, s), 7.58 (1H, d, J=5.1 Hz), 5.68 (1H, s), 5.05 (2H, s), 2.29 (3H, s), 2.16 (3H, s). Physical property: oil.

EXAMPLE 21

N-(3-Methyl-[1,2,4]oxadiazol-5-yl)-4-(trifluoromethyl)nicotinamide (Compound No. 2-2)

$^1$H-NMR (DMSO-d$_6$) δ (ppm): 8.70–9.10 (2H, brd.s), 7.72 (1H, brd.s), 2.16 (3H, brd.s). Physical property: oil.

EXAMPLE 22

N-(4-Chloro-3-cyano-5-isoxazolyl)-4-(trifluoromethyl)nicotinamide (Compound No. 1-36)

$^1$H-NMR (CDCl$_3$) δ (ppm): 9.05–8.95 (2H, m), 7.71 (1H, d, J=5.1 Hz). Physical property: amorphous.

EXAMPLE 23

N-(4-Fluoro-3-cyano-5-isoxazolyl)-4-(trifluoromethyl)nicotinamide (Compound No. 1-38)

$^1$H-NMR (DMSO-d$_6$) δ (ppm): 11.98 (1H, s), 9.10–9.03 (3H, m), 7.95 (1H, d, J=5.2 Hz). Melting point: 122–123° C.

EXAMPLE 24

N-(4-Bromo-5-isoxazolyl)-4-(trifluoromethyl)nicotinamide (Compound No. 1-40)

$^1$H-NMR (CDCl$_3$) δ (ppm): 8.96 (1H, s), 8.94 (1H, d, J=5.1 Hz), 8.26 (1H, s), 8.16 (1H, s), 7.68 (1H, d, J=5.1 Hz). Melting point: 98–100° C.

EXAMPLE 25

N-(4-Iode-5-isoxazolyl)-4-(trifluoromethyl)nicotinamide (Compound No. 1-42)

$^1$H-NMR (CDCl$_3$) δ (ppm): 8.99–8.96 (2H, m), 8.24 (1H, s), 7.91 (1H, brd.s), 7.69 (1H, d, J=5.5 Hz). Melting point: 176–178° C.

EXAMPLE 26

N-(3-Diethoxymethyl-5-isoxazolyl)-4-(trifluoromethyl)nicotinamide (Compound No. 1-56)

$^1$H-NMR (CDCl$_3$) δ (ppm): 9.80 (1H, brd.s), 8.91 (1H, s), 8.90 (1H, d, J=5.1 Hz), 7.68 (1H, d, J=5.1 Hz), 6.64 (1H, s), 5.55 (1H, s), 3.80–3.55 (4H, m), 1.25 (6H, t, J=7.0 Hz). Physical property: amorphous.

EXAMPLE 27

N-Acetyl-N-(3-methyl-5-isoxazolyl)-4-(trifluoromethyl)nicotinamide (Compound No. 1-57)

$^1$H-NMR (CDCl$_3$) δ (ppm): 8.85 (1H, d, J=5.1 Hz), 8.75 (1H, s), 7.57 (1H, d, J=5.1 Hz), 6.17 (1H, s), 2.35 (3H, s), 2.31 (3H, s). Physical property: oil.

EXAMPLE 28

N-(3-Methoxyiminomethyl-5-isoxazolyl)-4-(trifluoromethyl)nicotinamide (Compound No. 1-58)

$^1$H-NMR (CDCl$_3$) δ (ppm): 8.84 (1H, s), 8.79 (1H, d, J=5.1 Hz), 7.94 (1H, s), 7.66 (1H, d, J=5.1 Hz), 6.81 (1H, s), 4.02 (3H, s). Melting point: 140–144° C.

EXAMPLE 29

N-(3-Ethoxycarbonyl-5-isoxazolyl)-4-(trifluoromethyl)nicotinamide (Compound No. 1-59)

$^1$H-NMR (CDCl$_3$) δ (ppm): 8.94 (1H, s), 8.90 (1H, d, J=5.1 Hz), 7.67 (1H, d, J=5.1 Hz), 6.92 (1H, s), 4.43 (2H, q, J=7.3 Hz), 1.41 (3H, t, J=7.3 Hz). Physical property: amorphous.

EXAMPLE 30

5-[N,N-Bis(4-trifluoromethylnicotinoyl)]aminoisoxazole (Compound No. 1-60)

$^1$H-NMR (DMSO-d$_6$) δ (ppm): 9.30 (1H, s), 9.14 (1H, d, J=4.9 Hz), 9.01 (2H, m), 7.98 (1H, d, J=5.2 Hz), 7.91 (1H, d, J=5.2 Hz), 7.78 (1H, d, J=10.2 Hz), 5.09 (1H, t, J=9.9 Hz). Physical property: amorphous.

EXAMPLE 31

N-Ethoxymethyl-N-(4-iode-5-isoxazolyl)-4-(trifluoromethyl)nicotinamide (Compound No. 1-61)

$^1$H-NMR (CDCl$_3$) δ (ppm): 8.79 (1H, d, J=4.8 Hz), 8.66 (1H, s), 8.11 (1H, s), 7.57 (1H, d, J=5.1 Hz), 5.38 (2H, brd.s), 3.79 (2H, d, J=7.0 Hz), 1.24 (3H, t, J=7.1 Hz). Melting point: 114–116° C.

EXAMPLE 32

N-(4-Methyl-5-isoxazolyl)-4-(trifluoromehyl)nicotinamide (Compound No. 1-62)

$^1$H-NMR (CDCl$_3$) δ (ppm): 11.52 (1H, s), 9.09 (1H, s), 9.02 (1H, d, J=5.1 Hz), 8.49 (1H, s), 7.94 (1H, d, J=5.1 Hz), 1.95 (3H, s). Melting point: 115–116° C.

EXAMPLE 33

N-(3,4-Dimethyl-5-isoxazolyl)-4-(trifluoromethyl)nicotinamide (Compound No. 1-63)

$^1$H-NMR (CDCl$_3$) δ (ppm): 9.43 (1H, brd.s), 8.88–8.79 (2H, m), 7.63 (1H, d, J=5.1 Hz), 2.17 (3H, s), 1.95 (3H, s). Melting point: 141–143° C.

EXAMPLE 34

N-(4-Ethyl-5-isoxazolyl)-4-(trifluoromethyl)nicotinamide (Compound No. 1-64)

$^1$H-NMR (CDCl$_3$) δ (ppm): 8.91 (1H, s), 8.90 (1H, d, J=5.1 Hz), 8.65 (1H, brd.s), 8.14 (1H, s), 7.66 (1H, d, J=5.1 Hz), 2.50 (2H, q, J=7.7 Hz), 1.21 (3H, t, J=7.7 Hz). Melting point: 136–137° C.

EXAMPLE 35

N-(4-Propyl-5-isoxazolyl)-4-(trifluoromethyl)nicotinamide (Compound No. 1-65)

$^1$H-NMR (CDCl$_3$) δ (ppm): 8.90 (1H, s), 8.88 (1H, d, J=5.1 Hz), 8.11 (1H, s), 7.65 (1H, d, J=5.1 Hz), 2.51–2.31 (2H, m), 1.65–1.54 (2H, m), 0.96 (3H, t, J=7.3 Hz). Melting point: 120–123° C.

EXAMPLE 36

N-(4-Isopropyl-5-isoxazolyl)-4-(trifluoromethyl)nicotinamide (Compound No. 1-66)

$^1$H-NMR (CDCl$_3$) δ (ppm): 8.87 (1H, s), 8.85 (1H, d, J=5.1 Hz), 8.13 (1H, s), 7.64 (1H, d, J=5.1 Hz), 3.00–2.93 (1H, m), 1.21 (6H, d, J=7.0 Hz). Physical property: oil.

EXAMPLE 37

N-(4-Cyclopropyl-5-isoxazolyl)-4-(trifluoromethyl)nicotinamide (Compound No. 1-67)

$^1$H-NMR (CDCl$_3$) δ (ppm): 8.93 (1H, s), 8.92 (1H, d, J=5.1 Hz), 8.40 (1H, brd.s), 7.94 (1H, s), 7.67 (1H, d, J=5.1 Hz), 1.88–1.55 (1H, m), 1.05–0.80 (2H, m), 0.65–0.45 (2H, m). Melting point: 140–141° C.

EXAMPLE 38

N-(4-Allyl-5-isoxazolyl)-4-(trifluoromethyl)nicotinamide (Compound No. 1-68)

$^1$H-NMR (CDCl$_3$) δ (ppm): 8.93 (1H, s), 8.92 (1H, d, J=5.1 Hz), 8.12 (1H, s), 7.67 (1H, d, J=5.1 Hz), 6.05–5.75 (1H, m), 5.20–5.00 (2H, m), 3.26 (2H, d, J=5.9 Hz). Melting point: 93–97° C.

EXAMPLE 39

N-(4-Butyl-5-isoxazolyl)-4-(trifluoromethyl)nicotinamide (Compound No. 1-69)

$^1$H-NMR (CDCl$_3$) δ (ppm): 9.02 (1H, brd.s), 8.89 (1H, s), 8.87 (1H, d, J=5.1 Hz), 8.10 (1H, s), 7.65 (1H, d, J=5.1 Hz), 2.45 (2H, t, J=7.0 Hz), 1.65–1.20 (4H, m), 0.93 (3H, t, J=7.0 Hz). Melting point: 86–88° C.

EXAMPLE 40

N-(4-Isobutyl-5-isoxazolyl)-4-(trifluoromethyl)nicotinamide (Compound No. 1-70)

$^1$H-NMR (CDCl$_3$) δ (ppm): 8.91 (1H, s), 8.90 (1H, d, J=5.1 Hz) 8.71 (1H, brd.s), 8.10 (1H, s), 7.66 (1H, d, J=5.1 Hz), 2.36 (2H, d, J=7.0 Hz), 1.95–1.70 (1H, m), 0.93 (6H, d, J=7.0 Hz). Melting point: 81–84° C.

EXAMPLE 41

N-(4-Cyclobutyl-5-isoxazolyl)-4-(trifluoromethyl)nicotinamide (Compound No. 1-71)

$^1$H-NMR (CDCl$_3$) δ (ppm): 9.10–8.60 (3H, m), 8.21 (1H, s), 7.65 (1H, d, J=5.1 Hz), 3.60–3.30 (1H, m), 2.45–1.60 (6H, m). Melting point: 132–135° C.

EXAMPLE 42

N-(4-Cyclopentyl-5-isoxazolyl)-4-(trifluoromethyl)nicotinamide (Compound No. 1-72)

$^1$H-NMR (CDCl$_3$) δ (ppm): 8.93 (1H, s), 8.92 (1H, d, J=5.1 Hz), 8.39 (1H, brd.s), 8.16 (1H, s), 7.68 (1H, d, J=5.1 Hz), 3.10–2.80 (1H, m), 2.20–1.30 (8H, m). Melting point: 132–133° C.

EXAMPLE 43

N-(4-Hexyl-5-isoxazolyl)-4-(trifluoromethyl)nicotinamide (Compound No. 1-73)

$^1$H-NMR (CDCl$_3$) δ (ppm): 8.91 (1H, s), 8.89 (1H, d, J=5.1 Hz), 8.12 (1H, s), 7.66 (1H, d, J=5.1 Hz), 2.45 (2H, brd.t, J=7.0 Hz), 1.70–1.15 (8H, m), 0.89 (3H, t, J=7.0 Hz). Melting point: 38–40° C.

EXAMPLE 44

5-[N,N-Bis(4-trifluoromethylnicotinoyl)]amino-4-hexylisoxazole (Compound No. 1-74)

$^1$H-NMR (CDCl$_3$) δ (ppm): 9.20–8.70 (4H, m), 7.95–7.50 (3H, m), 2.40–2.00 (2H, m), 1.70–1.10 (8H, m), 1.00–0.70 (3H, m). Melting point: 71–74° C.

EXAMPLE 45

N-(4-Benzyl-5-isoxazolyl)-4-(trifluoromethyl)nicotinamide (Compound No. 1-75)

$^1$H-NMR (CDCl$_3$) δ (ppm): 8.77 (1H, d, J=5.1 Hz), 8.56 (1H, s), 7.95 (1H, s), 7.59 (1H, d, J=5.1 Hz), 7.40–7.05 (5H, m), 3.83 (2H, s). Physical property: oil.

EXAMPLE 46

N-(4-Phenylethyl-5-isoxazolyl)-4-(trifluoromethyl)nicotinamide (Compound No. 1-76)

$^1$H-NMR (CDCl$_3$) δ (ppm): 8.85 (1H, d, J=5.1 Hz), 8.76 (1H, s), 8.64 (1H, brd.s), 7.94 (1H, s), 7.63 (1H, d, J=5.1 Hz), 7.35–7.05 (5H, m), 2.95–2.65 (4H, m). Physical property: amorphous.

EXAMPLE 47

N-(4-Methoxy-5-isoxazolyl)-4-(trifluoromethyl)nicotinamide (Compound No. 1-77)

$^1$H-NMR (DMSO-d$_6$) δ (ppm): 11.32 (1H, s), 9.04–9.00 (2H, m), 8.85 (1H, s), 7.94 (1H, d, J=4.6 Hz), 3.82 (3H, s). Melting point: 123–125° C.

EXAMPLE 48

N-(4-Methoxy-3-methoxymethyl-5-isoxazolyl)-4-(trifluoromethyl)nicotinamide (Compound No. 1-78)

$^1$H-NMR (CDCl$_3$) δ (ppm): 8.96–8.94 (2H, m), 7.84 (1H, brd.s), 7.67 (1H, d, J=4.6 Hz), 4.50 (2H, s), 3.92 (3H, s), 3.41 (3H, s). Melting point: 144–146° C.

EXAMPLE 49

N-(4-Methylthio-5-isoxazolyl)-4-(trifluoromethyl)nicotinamide (Compound No. 1-79)

$^1$H-NMR (CDCl$_3$) δ (ppm): 8.97–8.94 (2H, m), 8.25 (1H, s), 7.68 (1H, d, J=5.5 Hz), 2.32 (3H, s) Melting point: 127–129° C.

EXAMPLE 50

5-[N,N-Bis(4-trifluoromethylnicotinoyl)]amino-4-methylthioisoxazole (Compound No. 1-80)

$^1$H-NMR (CDCl$_3$) δ (ppm): 8.93–8.89 (4H, m), 8.22 (1H, s), 7.65–7.62 (2H, m), 2.41 (3H, s). Physical property: amorphous.

EXAMPLE 51

N-(4-Phenoxy-5-isoxazolyl)-4-(trifluoromethyl)nicotinamide (Compound No. 1-81)

$^1$H-NMR (CDCl$_3$) δ (ppm): 8.84 (1H, d, J=5.5 Hz), 8.71 (1H, s) 8.26 (1H, s), 7.59 (1H, d, J=5.5 Hz), 7.37–7.26 (3H, m), 7.15–7.08 (2H, m), 6.99 (1H, brd.s). Physical property: oil.

EXAMPLE 52

5-[N,N-Bis(4-trifluoromethylnicotinoyl)]amino-4-phenoxyisoxazole (Compound No. 1-82)

$^1$H-NMR (CDCl$_3$) δ (ppm): 8.91–8.84 (4H, m), 8.10 (1H, s), 7.62–7.60 (2H, m), 7.39–7.31 (3H, m), 7.21–7.14 (1H, m), 6.99–6.93 (2H, m). Physical property: oil.

EXAMPLE 53

N-(4-Phenyl-5-isoxazolyl)-4-(trifluoromethyl)nicotinamide (Compound No. 1-83)

$^1$H-NMR (CDCl$_3$) δ (ppm): 8.90–8.87 (2H, m), 8.41 (1H, s), 8.21 (1H, brd.s), 7.63 (1H, d, J=5.1 Hz), 7.48–7.36 (5H, m). Melting point: 152–155° C.

EXAMPLE 54

N-[4-(4-Methylphenyl)-5-isoxazolyl]-4-(trifluoromethyl)nicotinamide (Compound No. 1-84)

$^1$H-NMR (CDCl$_3$) δ (ppm): 8.90–8.88 (2H, m), 8.39 (1H, s), 7.63 (1H, d, J=4.9 Hz), 7.32–7.21 (4H, m), 2.37 (3H, s). Melting point: 155–157° C.

EXAMPLE 55

N-[4-(4-Methoxyphenyl)-5-isoxazolyl]-4-(trifluoromethyl)nicotinamide (Compound No. 1-85)

$^1$H-NMR (CDCl$_3$) δ (ppm): 8.90–8.89 (2H, m), 8.44 (1H, brd.s), 8.38 (1H, s), 7.64 (1H, d, J=5.1 Hz), 7.36–7.31 (2H, m), 6.99–6.93 (2H, m), 3.83 (3H, s). Melting point: 77–79° C.

EXAMPLE 56

N-[4-(4-Chlorophenyl)-5-isoxazolyl]-4-(trifluoromethyl)nicotinamide (Compound No. 1-86)

$^1$H-NMR (CDCl$_3$) δ (ppm): 8.93–8.91 (2H, m), 8.63 (1H, brd.s), 8.42 (1H, s), 7.65 (1H, d, J=4.9 Hz), 7.42–7.26 (4H, m). Melting point: 166–168° C.

EXAMPLE 57

N-[4-(4-Trifluoromethylphenyl)-5-isoxazolyl]-4-(trifluoromethyl)nicotinamide (Compound No. 1-87)

$^1$H-NMR (CDCl$_3$) δ (ppm): 8.95–8.92 (2H, m), 8.48 (1H, s), 7.71–7.65 (3H, m), 7.53 (2H, d, J=8.4 Hz). Melting point: 128–130° C.

EXAMPLE 58

N-[4-(4-Trifluoromethoxyphenyl)-5-isoxazolyl]-4-(trifluoromethyl)nicotinamide (Compound No. 1-88)

$^1$H-NMR (CDCl$_3$) δ (ppm): 8.93–8.91 (2H, m), 8.42 (1H, s), 8.27 (1H, brd.s), 7.66 (1H, d, J=5.5 Hz), 7.46–7.42 (2H, m), 7.30–7.26 (2H, m). Melting point: 161–163° C.

EXAMPLE 59

N-[4-(3-Pyridyl)-5-isoxazolyl]-4-(trifluoromethyl)nicotinamide (Compound No. 1-89)

$^1$H-NMR (CDCl$_3$) δ (ppm): 8.93–8.84 (2H, m), 8.57–8.56 (1H, brd.s), 8.43–8.39 (2H, m), 7.76–7.71 (1H, m), 7.62–7.60 (1H, d, J=5.2 Hz), 7.36–7.31 (1H, m). Physical property: amorphous.

EXAMPLE 60

N-(4-Chloro-3-methoxyiminomethyl-5-isoxazolyl)-4-(trifluoromethyl)nicotinamide (Compound No. 1-90)

$^1$H-NMR (CDCl$_3$) δ (ppm): 8.94–8.88 (2H, m), 8.05 (1H, s), 7.65 (1H, d, J=5.1 Hz), 4.05 (3H, s). Physical property: amorphous.

EXAMPLE 61

N-(3-Methyl-4-phenyl-5-isoxazolyl)-4-(trifluoromethyl)nicotinamide (Compound No. 1-91)

$^1$H-NMR (CDCl$_3$) δ (ppm): 8.87 (1H, d, J=5.3 Hz), 8.78 (1H, brd.s), 8.04 (1H, s), 7.60 (1H, d, J=5.3 Hz), 7.48–7.30 (5H, m), 2.29 (3H, s). Melting point: 155–157° C.

EXAMPLE 62

N-[4-(Cyclohex-1-ene-1-yl)-5-isoxazolyl]-4-(trifluoromethyl)nicotinamide (Compound No. 1-92)

$^1$H-NMR (CDCl$_3$) δ (ppm): 8.92 (2H, brd m), 8.20 (2H, brd m), 7.65 (1H, d, J=4.6 Hz), 5.97–5.94 (1H, m), 2.24–2.16 (4H, m), 1.76–1.62 (4H, m). Melting point: 161–163° C.

EXAMPLE 63

N-(4-Methoxymethyl-5-isoxazolyl)-4-(trifluoromethyl)nicotinamide (Compound No. 1-93)

$^1$H-NMR (CDCl$_3$) δ (ppm): 8.99–8.95 (2H, m), 8.60 (1H, s), 8.22 (1H, s), 7.68 (1H, d, J=4.9 Hz), 4.44 (2H, s), 3.40 (3H, s). Physical property: amorphous.

EXAMPLE 64

N-[4-(1H-Pyrazol-1-yl)-5-isoxazolyl]-4-(trifluoromethyl)nicotinamide (Compound No. 1-94)

$^1$H-NMR (CDCl$_3$) δ (ppm): 10.55 (1H, brd s), 9.06–8.06 (2H, m), 8.51 (1H, s), 7.74–7.65 (3H, m), 6.48–6.45 (1H, m). Physical property: amorphous.

EXAMPLE 65

N-(4-Cyclohexyl-5-isoxazolyl)-4-(trifluoromethyl)nicotinamide (Compound No. 1-95)

$^1$H-NMR (CDCl$_3$) δ (ppm): 8.93–8.91 (2H, m), 8.22 (1H, brd.s), 8.17 (1H, s), 7.66 (1H, d, J=5.2 Hz), 2.66–2.52 (1H, m), 1.91–1.68 (4H, m), 1.43–1.22 (6H, m). Melting point: 125–127° C.

EXAMPLE 66

N-(4-Fluoro-3-methyl-5-isoxazolyl)-4-(trifluoromethyl)nicotinamide (Compound No. 1-39)

$^1$H-NMR (DMSO-d$_6$) δ (ppm): 11.90 (1H, s), 9.09 (1H, s), 9.03 (1H, d, J=5.1 Hz), 7.95 (1H, d, J=5.1 Hz), 2.30 (3H, s) Melting point: 122–124° C.

REFERENCE EXAMPLE 1

3-[(4,4,4-Trifluoro-3-oxo-1-butenyl)amino]-2-propenenitrile (Compounds IIa and IIb, Step D)

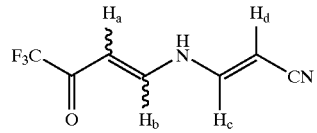

(IIa)

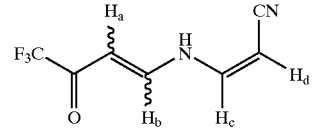

(IIb)

Sodium hydride (60% dispersion in mineral oil, 400 mg, 10 mmol) was charged and washed with hexane twice. Into this flask, N,N-dimethylformamide (10 ml) was added and then a solution prepared by dissolving 4-amino-1,1,1-trifluoro-3-buten-2-one (1.4 g, 10 mmol) and 3-methoxyacrylonitrile (830 mg, 10 mmol) in N,N-dimethylformamide (5 ml) was added dropwise under ice-cooling. After stirring the mixture at room temperature for 3 hours, the reaction mixture was poured into water (50 ml). This mixture was acidified with concentrated hydrochloric acid under ice-cooling, and then extracted with ethyl acetate. The organic layers were combined, washed with brine, dried over magnesium sulfate and then concentrated under reduced pressure. The resulting residue was purified by silica gel column chromatography (an eluting solvent: hexane/ethyl acetate=3/1 to 1/1) to obtain 993 mg (yield 52.3%) of title compound (IIa) having a low polarity and 457 mg (yield 24.0%) of title compound (IIb) having a high polarity.

Low-polar compound (IIa, a mixture of two types of geometrical isomers) (Rf=0.38; a developing solvent: hexane/ethyl acetate=2/1)

$^1$H-NMR spectrum (200 MHz, CD$_3$OD) δ (ppm) Ha: 5.90 (0.65H, d, J=13.2 Hz); 5.68 (0.35H, d, J=8.1 Hz) Hb: 7.93 (0.65H, d, J=13.2 Hz); 7.43 (0.35H, d, J=8.1 Hz) Hc: 7.53 (0.65H, d, J=13.9 Hz); 7.42 (0.35H, d, J=13.9 Hz) Hd: 5.44 (0.35H, d, J=13.9 Hz); 5.00 (0.65H, d, J=13.9 Hz) MS (EI): M/Z: 190 (M$^+$), 162, 147, 133, 121.

High-polar compound (IIb, a mixture of two types of geometrical isomers) (Rf=0.16; a developing solvent: hexane/ethyl acetate=2/1)

$^1$H-NMR spectrum (200 MHz, CD$_3$OD) δ (ppm) Ha: 6.11 (0.5H, d, J=13.2 Hz), 5.78 (0.5H, d, J=7.7 Hz) Hb: 7.94 (0.5H, d, J=13.2 Hz), 7.59 (0.5H, d, J=7.7 Hz) Hc: 7.32 (0.5H, d, J=8.4 Hz); 7.24 (0.5H, d, J=8.8 Hz) Hd: 4.95 (0.5H, d, J=8.4 Hz); 4.75 (0.5H, d, J=8.8 Hz) MS (EI): M/Z: 190 (M$^+$), 151, 129, 121.

REFERENCE EXAMPLE 2

3-[(4,4,4-Trifluoro-3-oxo-1-butenyl)amino]-2-propenenitrile (Compounds IIa and IIb, Step D)

Sodium hydride (60% dispersion in mineral oil, 400 mg, 10 mmol) was charged and washed with hexane twice. Into this flask, 1,2-dimethoxyethane (20 ml) was added and then a solution prepared by dissolving 4-amino-1,1,1-trifluoro-3-buten-2-one (1.4 g, 10 mmol) and 3-methoxyacrylonitrile (830 mg, 10 mmol) in 1,2-dimethoxyethane (5 ml) was added dropwise under ice-cooling. After stirring the mixture at room temperature for 4 hours, the reaction mixture was poured into water (50 ml). This mixture was acidified with concentrated hydrochloric acid under ice-cooling and then extracted with ethyl acetate. The organic layers were combined, washed with saturated brine, dried over magnesium sulfate and then concentrated under reduced pressure. The resulting residue was purified by silica gel column chromatography (a eluting solvent: hexane/ethyl acetate=3/1 to 1/1) to obtain 593 mg (yield 31.2%) of title compound (IIa) having a low polarity and 680 mg (yield 35.8%) of title compound (IIb) having a high polarity.

REFERENCE EXAMPLE 3

3-[(4,4,4-Trifluoro-3-oxo-1-butenyl)amino]-2-propenenitrile (Compounds IIa and IIb, Step D)

Sodium hydride (60% dispersion in mineral oil suspension, 4.00 g, 100 mmol) was added and washed with hexane twice. Into this flask, N,N-dimethylformamide (100 ml) was added and then a solution prepared by dissolving 4-amino-1,1,1-trifluoro-3-buten-2-one (13.9 g, 100 mmol) and 3-methoxyacrylonitrile (8.30 g, 100 mmol) in N,N-dimethylformamide (50 ml) was added dropwise under ice-cooling. After stirring the mixture at room temperature for 3 hours, the reaction mixture was poured into water (500 ml). This mixture was acidified with concentrated hydrochloric acid under ice-cooling, the precipitate was collected by filtration and then washed with cold water. The obtained precipitate was dried under reduced pressure to obtain 8.20 g (yield 43.1%) of a mixture of compounds (IIa) and (IIb).

REFERENCE EXAMPLE 4

3-[(4,4,4-Trifluoro-3-oxo-1-butenyl)amino]-2-propenenitrile (Compounds IIa and IIb, Step E)

Sodium hydride (60% dispersion in mineral oil, 400 mg, 10 mmol) was charged and washed with hexane twice. Into this flask, N,N-dimethylformamide (15 ml) was added and a solution prepared by dissolving 4-amino-1,1,1-trifluoro-3-buten-2-one (1.4 g, 10 mmol) and. 3,3-dimethoxypropionitrile (1.15 g, 10 mmol) in N,N-dimethylformamide (5 ml) was added dropwise under ice-cooling. After stirring the mixture at room temperature for 4 hours, the reaction mixture was poured into water (50 ml). This mixture was acidified with concentrated hydrochloric acid and then extracted with ethyl acetate. The organic layers were combined, washed with brine, dried over magnesium sulfate and then concentrated under reduced pressure. The resulting residue was purified by silica gel column chromatography (a eluting solvent: hexane/ethyl acetate=3/1 to 1/1) to obtain 251 mg (yield 13.2%) of title compound (IIa) having a low polarity and 372 mg (yield 19.8%) of title compound (IIb) having a high polarity.

REFERENCE EXAMPLE 5

3-Cyano-4-trifluoromethylpyridine (Compound VIIb, Step F)

To a solution of 28% sodium methoxide (580 mg, 3.0 mmol), a solution prepared by dissolving 3-[(4,4,4-trifluoro-3-oxo-1-butenyl)amino]-2-propenenitrile (a mixture of IIa and IIb; 380 mg, 2.0 mmol) in methanol (5 ml) was added at room temperature and then, the mixture was refluxed for 2 hours. The reaction solution was poured into water and extracted with ethyl acetate. The organic layers were combined, washed with brine, dried over magnesium sulfate and then concentrated. The resulting residue was purified by silica gel column chromatography (a eluting solvent: hexane/ethyl acetate=3/1) to obtain 195 mg (yield 56.5%) of the title compound.

$^1$H-NMR spectrum (200 MHz, CD$_3$OD) δ (ppm) 9.11 (1H, s), 9.03 (1H, d, J=5.1 Hz), 7.72 (1H, d, J=5.1 Hz).

REFERENCE EXAMPLE 6

3-Cyano-4-trifluoromethylpyridine (Compound VIIb, Step F)

To a solution of 28% sodium methoxide (290 mg, 1.5 mmol), a solution prepared by dissolving 3-[(4,4,4-trifluoro-3-oxo-1-butenyl)amino]-2-propenenitrile (a low-polar compound IIa; 190 mg, 1.0 mmol) in methanol (2 ml) was added at room temperature and then, the mixture was refluxed for 2 hours. The reaction solution was poured into water and extracted with ethyl acetate. The organic layers were combined, washed with brine, dried over magnesium sulfate and then concentrated. The resulting residue was purified by thin layer chromatography (a developing solvent: hexane/ethyl acetate=3/1) to obtain 71.0 mg (yield 41.5%) of the title compound.

REFERENCE EXAMPLE 7

3-Cyano-4-trifluoromethylpyridine (Compound VIIb, Step F)

To a solution of 28% sodium methoxide (290 mg, 1.5 mmol), a solution prepared by dissolving 3-[(4,4,4-trifluoro-3-oxo-1-butenyl)amino]-2-propenenitrile (a high-polar compound IIb; 190 mg, 1.0 mmol) in methanol (2 ml) was added at room temperature and then, the mixture was refluxed for 2 hours. The reaction solution was poured into water and extracted with ethyl acetate. The organic layers were combined, washed with brine, dried over magnesium sulfate and then concentrated. The resulting residue was purified by thin layer chromatography (a developing solvent: hexane/ethyl acetate=3/1) to obtain 81.0 mg (yield 47.2%) of the title compound.

REFERENCE EXAMPLE 8

4-Trifluoromethylnicotinamide (Compound VIIc, Step F)

3-[(4,4,4-Trifluoro-3-oxo-1-butenyl)amino]-2propenenitrile (a mixture of IIa and IIb; 1.90 g, 10 mmol) was dissolved in methanol (15 ml), and sodium hydroxide (600 mg, 15 mmol) was added. The mixture was heated under reflux for 6 hours. The reaction mixture was concentrated under reduced pressure. The resulting residue was purified by silica gel column chromatography (a eluting solvent: hexane/acetone=1/1) to obtain 1.25 g (yield 65.6%) of the title compound.
$^1$H-NMR spectrum (200 MHz, DMSO-$d_6$) δ (ppm) 8.89 (1H, d, J=5.1 Hz), 8.82 (1H, s), 8.18 (1H, brs), 7.85 (1H, brs), 7.81 (1H, d, J=5.1 Hz).

REFERENCE EXAMPLE 9

4-Trifluoromethylnicotinamide (Compound VIIc, Step F)

3-[(4,4,4-Trifluoro-3-oxo-1-butenyl)amino]-2-propenenitrile (a low-polar compound IIa; 1.90 g, 10 mmol) was dissolved in methanol (15 ml), and sodium hydoxide (600 mg, 15 mmol) was added. The mixture was heated under reflux for 6 hours. The reaction mixture was concentrated under reduced pressure. The resulting residue was purified by silica gel column chromatography (a eluting solvent: hexane/acetone=1/1) to obtain 1.25 g (yield 65.6%) of the title compound.

REFERENCE EXAMPLE 10

4-Trifluoromethylnicotinamide (Compound VIIc, Step F)

3-[(4,4,4-Trifluoro-3-oxo-1-butenyl)amino]-2-propenenitrile (a high-polar compound IIb; 2.10 g, 11 mmol) was dissolved in methanol (15 ml), and sodium hydroxide (680 mg, 17 mmol) was added. The mixture was heated under reflux for 6 hours. The reaction solution was concentrated under reduced pressure. The resulting residue was purified by silica gel column chromatography (a eluting solvent: hexane/acetone=1/1) to obtain 1.26 g (yield 60.1%) of the title compound.

REFERENCE EXAMPLE 11

4-Trifluoromethylnicotinamide (Compound VIIc, Step F)

3-[(4,4,4-Trifluoro-3-oxo-1-butenyl)amino]-2-propenenitrile (a mixture of IIa and IIb; 1.90 g, 10 mmol) was dissolved in ethanol (15 ml), and sodium hydroxide (600 mg, 17 mmol) was added. The mixture was heated under reflux for 8 hours. The reaction solution was concentrated under reduced pressure. The resulting residue was purified by silica gel column chromatography (a eluting solvent: hexane/acetone=1/1) to obtain 0.53 g (yield 26.5%) of the title compound.

REFERENCE EXAMPLE 12

4-Trifluoromethylnicotinamide (Compound VIIc, Step F)

3-[(4,4,4-Trifluoro-3-oxo-1-butenyl)amino]-2-propenenitrile (a mixture of IIa and IIb; 1.90 g, 10 mmol) was dissolved in methanol (15 ml), and potassium hydroxide (990 mg, 15 mmol) was added. The mixture was heated under reflux for 6 hours. The reaction solution was concentrated under reduced pressure. The resulting residue was purified by silica gel column chromatography (a eluting solvent: hexane/acetone=1/1) to obtain 1.03 g (yield 52.6%) of the title compound.

REFERENCE EXAMPLE 13

3-Cyano-4-trifluoromethylpyridine (Compound VIIb, Step F)

3-[(4,4,4-Trifluoro-3-oxo-1-butenyl)amino]-2-propenenitrile (a mixture of IIa and IIb; 1.90 g, 10 mmol) was dissolved in methanol (20 ml), and potassium carbonate (2.10 g, 15 mmol) was added. The mixture was heated under reflux for 2 hours. The reaction solution was concentrated under reduced pressure. The resulting residue was purified by silica gel column chromatography (a eluting solvent: hexane/ethyl acetate=3/1) to obtain 653 mg (yield 32.7%) of the title compound.

REFERENCE EXAMPLE 14

4-Trifluoromethylnicotinic acid (Compound VIII)

5 ml of 35% concentrated hydrochloric acid (10 ml, 57 mmol) was added to 4-trifluoromethylnicotinamide (90 g, 10 mmol), and the mixture was heated under reflux for 5 hours.

Water (50 ml) was added, and the mixture was adjusted to pH 3 using sodium carbonate, and then extracted with ethyl acetate twice. The organic layers were combined, dried over magnesium sulfate and then concentrated under reduced pressure to obtain 1.71 g (yield 89.7%) of the title compound.

$^1$H-NMR spectrum (500 MHz, DMSO-$d_6$) δ (ppm) 14.07 (1H, brd.s), 9.08 (1H, s), 9.00 (1H, d, J=5.2 Hz), 7.89 (1H, d, J=5.2 Hz).

REFERENCE EXAMPLE 15

4-Trifluoromethylnicotinic acid (Compound VIII)

3-Cyano-4-trifluoromethylpyridine (11.47 g, 66.64 mmol) was suspended in ethylene glycol (76 ml) and 85% potassium hydroxide (13.20 g, 200 mol) was added. The mixture was stirred under heating at 20° C. for 4 hours. The reaction solution was cooled to room temperature and then water (50 ml) and 4N hydrochloric acid (60 ml) were added. The resulting reaction mixture was extracted with ethyl acetate four times. The organic layers were combined, washed with saturated salt water, dried over magnesium sulfate, and then concentrated under reduced pressure to obtain 10.70 g (yield 84.0%) of the title compound.

REFERENCE EXAMPLE 16

4-Trifluoromethylnicotinic acid (Compound VIII)

To a suspension of sodium hydride (60% dispersion in mineral oil, 0.40 g, 10 mmol) in 10 ml of tetrahydrofuran, a tetrahydrofuran (2 ml) solution of 4-amino-1,1,1-trifluoromethyl-3-buten-2-one (1.39 g, 10 mmol) and 3-methoxyacrylonitrile (0.83 g, 10 mmol) was gradually added under ice-cooling. The mixture was stirred at the same temperature for 20 minutes and then stirred at room temperature for 3 hours. To the reaction mixture, concentrated hydrochloric acid (1.2 ml) was added and then the solvent was removed under reduced pressure. Ethyl acetate was added to the resulting residue. The organic layer was washed with brine twice, dried over magnesium sulfate and then concentrated. The residue was dissolved in methanol (20 ml) and 28% sodium methoxide (1.93 g, 10.0 mmol) was added. The mixture was refluxed for 3 hours. After removing methanol under reduced pressure, an 8N aqueous sodium hydroxide solution (5 ml, 40.0 mmol) was added to the reaction solution. The reaction mixture was refluxed for 5 hours, then poured into water, and the aqueous layer was washed with diethyl ether. The aqueous layer was acidified with concentrated hydrochloric acid and extracted with ethyl acetate twice. The obtained organic layer was washed with brine, dried over magnesium sulfate and then concentrated under reduced pressure to obtain 866 mg (yield 45.3%) of the title compound.

REFERENCE EXAMPLE 17

4-Trifluoromethylnicotinic acid chloride (Compound VIII)

4-Trifluoromethylnicotinic acid (50.09 g, 0.262 mol) was suspended in benzene (250 ml), and thionyl chloride (38.2 ml, 0.524 mol) and N,N-dimethylformamide (0.1 ml) were added. The mixture was refluxed for 3 hours. The reaction mixture was concentrated, and the residue was distilled under reduced pressure to obtain 49.45 g (yield 90.1%) of the title compound.

$^1$H-NMR spectrum (270 MHz, CDCl$_3$) δ (ppm) 9.32 (1H, s), 9.03 (1H, d, J=5.2 Hz), 7.71 (1H, d, J=5.2 Hz).

REFERENCE EXAMPLE 18

3-[(4,4,4-Trifluoro-3-oxo-1-butenyl)amino]-2-propenenitrile (Compounds IIa and IIb, Step E)

Sodium hydride (60% dispersion in mineral oil, 0.6 g, 15 mmol) was charged and washed with hexane twice. Into this flask, 1,3-dimethyl-2-imidazolydinone (20 ml) was added and a solution prepared by dissolving 4-amino-1,1,1-trifluoro-3-buten-2-one (2.1 g, 15 mmol) and 3-methoxyacrylonitrile (1.2 g, 15 mmol) in 1,3-dimethyl-2-imidazolydinone (5 ml) was added dropwise under ice-cooling. After stirring the mixture at room temperature for 3 hours, the reaction mixture was poured into water (200 ml). This mixture was acidified with concentrated hydrochloric acid under ice-cooling and then extracted with ethyl acetate. The obtained organic layers were washed with saturated brine, dried over magnesium sulfate and then concentrated under reduced pressure. The resulting residue was purified by silica gel column chromatography (a eluting solvent: hexane/ethyl acetate=3/1 to 2/1) to obtain 2.60 g (yield 92.0%) of a mixture of title compounds (IIa) and (IIb).

REFERENCE EXAMPLE 19

4-Trifluoromethyl nicotinate (Compound VIII)

To a solution of 28% sodium methoxide (193.0 g, 1.00 mol) in methanol (1.0 L), 4-amino-1,1,1-trifluoro-3-buten-2-one (159.6 g, 0.84 mmol) was added. The mixture was refluxed for 3 hours. After removing methanol from the mixture under reduced pressure, 8 mol/L of an aqueous sodium hydroxide solution (420 ml, 3.36 mol) was added to the mixture. The mixture was refluxed for 4 hours. The resulting reaction mixture was poured into water, and the aqueous layer was washed with diethyl ether. The aqueous layer was acidified with concentrated hydrochloric acid and extracted with ethyl acetate twice. The obtained organic layer was washed with brine, dried over magnesium sulfate and then concentrated under reduced pressure to obtain 112.8 g (yield 70.4%) of the title compound.

In the following Formulation Examples, the types and the proportions of the compounds and the adjuvants are not limited to these Examples and may be varied within wide ranges. In the following description, "%" means "% by mass".

FORMULATION EXAMPLE 1

Emulsifiable Concentrate

To the compound (5%) in Example 6, xylene (42.5%) and dimethylsulfoxide (42.5%) were added and dissolved. Subsequently, a mixture (mixing ratio: 8/2, 10%) of polyoxyethylene castor oil ether and calcium alkylbenzenesulfonate was mixed thereto to prepare an emulsifiable concentrate. The emulsifiable concentrate was diluted with water and used as a spray.

FORMULATION EXAMPLE 2

Wettable Powder

Into the compound (5%) in Example 6, kaolin (79%) and diatomaceous earth (10%) were mixed, and sodium lauryl sulfate (3%) and sodium lignin sulfonate (3%) were further mixed. The mixture was finely pulverized to obtain a wettable powder. The wettable powder was diluted with water and used as a spray.

FORMULATION EXAMPLE 3

Dust

To the compound (1%) in Example 6, a mixture (mixing ratio: 1/1, 99%) of talc and calcium carbonate was added and mixed. Then, the mixture was pulverized to prepare a dust. The dust was directly applied in use.

FORMULATION EXAMPLE 4

Granules

The compound (2%) in Example 6 was mixed with bentonite fine powder (30%), talc (66%) and sodium lignin sulfonate (2%). Then, the mixture was kneaded until it was made uniform, while adding thereto water. Next, the kneaded product was formed into granules through a granulator. The formed granule was passed through a sizer, a dehydrator and a sieve to prepare a granule having a particle size of 0.6 to 1.0 mm. The granule was directly applied on a soil surface in use.

FORMULATION EXAMPLE 5

Oil-based formuration

The compound (0.1%) in Example 6 was dissolved in illuminating kerosene to obtain 100% in total of an oil-based formuration.

TEST EXAMPLE 1

Insecticidal test for green peach aphid (*Myzus persicae*) (100 ppm)

Water (30 ml) was put into a beaker, and a leaf of Komatsuna (*Brassica* var. *rapa*) was placed within the beaker such that the stem was immersed in water. On the leaf of Komatsuna, five green peach aphids were released and allowed to fertilize. Two days after the releasing, imagoes were removed and the number of larvae was counted.

A surfactant Newcol NE-710F (trademark, produced by Nippon Nyukazai Co., Ltd., 2%) was dissolved in aqueous acetone (95% aqueous solution, 98%) to prepare solution 1. Next, a dispersant Gousenol GLO5-S (trademark, produced by Nippon Nyukazai Co., Ltd., 0.2% aqueous solution, 0.2%) was dissolved in water (99.8%) to prepare solution 2.

To each of the compounds (8 mg) of the present invention, the above solution 1 (0.4 ml), the above solution 2 (0.4 ml) and water (8 ml) were added. Further, the compounds of the present invention were each diluted with water so that the concentration of each compound was 100 ppm {as a spreading agent, Gramin S (trademark, produced by Sankyo Co., Ltd.) was added so as to have a concentration of 0.01%}.

The above chemical liquid (8 ml) was sprayed on the leaf of Komatsuna by use of a rotary spraying tower. The leaf of Komatsuna was put back in the beaker. Then, the beaker was placed in a thermostatic chamber of 25° C. for 16 hours in the light and for 8 hours in the dark. 5 Days after the spraying, the number of dead insects was counted to calculate the mortality (%).

As a result, the compounds in Example 1 (Compound No. 1-2), Example 2 (Compound No. 1-51), Example 3 (Compound No. 1-21), Example 4 (Compound No. 1-1), Example 5 (Compound No. 1-3), Example 6 (Compound No. 1-5), Example 7 (Compound No. 1-16), Example 8 (Compound No. 1-17), Example 9 (Compound No. 1-18), Example 10 (Compound No. 1-19), Example 11 (Compound No. 1-20), Example 12 (Compound No. 1-25), Example 13 (Compound No. 1-37), Example 14 (Compound No. 1-41), Example 15 (Compound No. 1-43), Example 16 (Compound No. 1-47), Example 18 (Compound No. 1-49), Example 19 (Compound No. 1-53), Example 20 (Compound No. 1-55), Example 21 (Compound No. 2-2), Example 22 (Compound No. 1-36), Example 23 (Compound No. 1-38), Example 24 (Compound No. 1-40), Example 25 (Compound No. 1-42), Example 26 (Compound No. 1-56), Example 27 (Compound No. 1-57), Example 28 (Compound No. 1-58), Example 29 (Compound No. 1-59), Example 30 (Compound No. 1-60), Example 31 (Compound No. 1-61), Example 32 (Compound No. 1-62), Example 33 (Compound No. 1-63), Example 34 (Compound No. 1-64), Example 35 (Compound No. 1-65), Example 36 (Compound No. 1-66), Example 37 (Compound No. 1-67), Example 38 (Compound No. 1-68), Example 39 (Compound No. 1-69), Example 40 (Compound No. 1-70), Example 41 (Compound No. 1-71), Example 42 (Compound No. 1-72), Example 43 (Compound No. 1-73), Example 44 (Compound No. 1-74), Example 45 (Compound No. 1-75), Example 46 (Compound No. 1-76), Example 47 (Compound No. 1-77), Example 48 (Compound No. 1-78), Example 49 (Compound No. 1-79), Example 50 (Compound No. 1-80), Example 51 (Compound No. 1-81), Example 52 (Compound No. 1-82), Example 53 (Compound No. 1-83), Example 54 (Compound No. 1-84), Example 55 (Compound No. 1-85), Example No. 56 (Compound No. 1-86), Example 57 (Compound No. 1-87), Example 58 (Compound No. 1-88), Example 59 (Compound No. 1-89), Example 60 (Compound No. 1-90), Example 61 (Compound No. 1-91), Example 62 (Compound No. 1-92), Example 63 (Compound No. 1-93), Example 64 (Compound No. 1-94), Example 65 (Compound No. 1-95) and Example 66 (Compound No. 1-39) showed the mortality (%) of 95% or more.

TEST EXAMPLE 2

Insecticidal Test for Green Peach Aphid (*Myzus persicae*) (10 ppm and 3 ppm)

The test was carried out in the same manner as in Test Example 1 except for setting the dilution concentration to 10 ppm and 3 ppm. Incidentally, Comparative Compound a and Comparative Compound b (Compound No. 6) listed in Table 1 of Japanese Provisional Patent Publication No. Hei 10-195072 were used as a comparison.

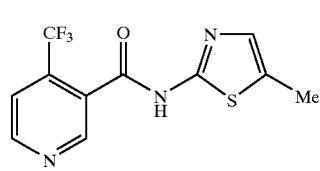

Comparative compound a

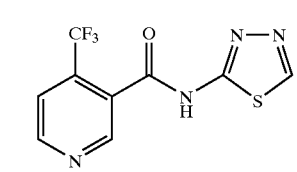

Comparative compound b

-continued

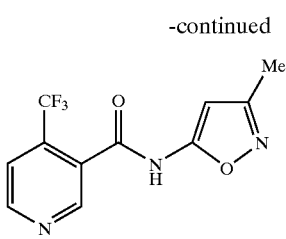

Compound No. 1-2

Example 1

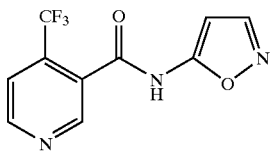

Compound No. 1-1

Example 4

The results are shown in Table 3.

TABLE 3

Insecticidal Test for Green Peach Aphid

| Test No. | Test Compound | Chemical Concentration of Spray | Mortality (%) | |
|---|---|---|---|---|
| | | | 10 ppm | 3 ppm |
| 1 | Compound in Example 1 | (Compound No. 1-2) | 100 | 100 |
| 2 | Compound in Example 4 | (Compound No. 1-1) | 100 | 100 |
| 3 | Comparative Compound a | | 6 | 0 |
| 4 | Comparative Compound b | | 0 | 0 |

INDUSTRIAL APPLICABILITY

The N-heteroaryl-4-(haloalkyl)nicotinamide derivative of the present invention exhibits excellent pesticidal activities against a wide range of pests such as hemipteran pest, lepidopteran pest, coleopteran pest, dipteran pest, hymenopteran pest, orthopteran pest, isopteran pest, thysanopteran pest, mites and plant-parastic nematodes pest.

Furthermore, by the present invention, compound (II) as an intermediate for the production of compounds useful as a starting material for producing pesticides or medicines can be inexpensively and simply produced in a high yield.

What is claimed is:

1. An N-heteroaryl-4-(haloalkyl)nicotinamide compound represented by formula (I):

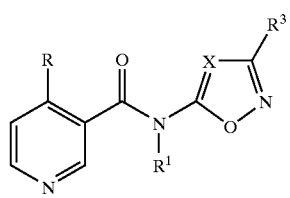

(I)

wherein R represents a $C_1-C_6$ alkyl group which is unsubstituted or substituted with 1 to 5 halogen atoms;

$R^1$ represents a hydrogen atom, a $C_1-C_6$ alkyl group which is unsubstituted or substituted with 1 to 5 substituents selected from the following substituent group A, a $C_2-C_6$ alkenyl group or an acyl group, the acyl group is an alkylcarbonyl group which is unsubstituted or substituted with a halogen atom or a lower alkoxy group; an aliphatic acyl group which is an unsaturated alkylcarbonyl group; an arylcarbonyl group which is unsubstituted or substituted with a halogen atom, a lower alkyl group, a lower alkoxy group, a nitro group, a lower alkoxycarbonyl group or an aryl group; a lower alkoxycarbonyl group which is unsubstituted or substituted with a halogen atom or a tri-lower alkylsilyl group; an alkenyloxycarbonyl group; an aralkyloxycarbonyl group which is unsubstituted or substituted with a lower alkoxy group or a nitro group; a lower alkanesulfonyl group which is unsubstituted or substituted with a halogen atom or a lower alkoxy group; or an arylsulfonyl group which is unsubstituted or substituted with a halogen atom, a lower alkyl group, a lower alkoxy group, a nitro group, a lower alkoxycarbonyl group or an aryl group;

X represents a group represented by formula C—$R^2$;

$R^2$ and $R^3$ each independently represent a hydrogen atom, a halogen atom, a $C_1-C_6$ alkyl group which is unsubstituted or substituted with 1 to 5 substituents selected from the following substituent group A, a $C_3-C_7$ cycloalkyl group, a $C_2-C_6$ alkenyl group, a $C_3-C_7$ cycloalkenyl group, a formyl group, a group represented by formula CH=$NOR^4$ (wherein $R^4$ is a hydrogen atom or a $C_1-C_6$ alkyl group), a cyano group, a phenyl group which is unsubstituted or substituted with 1 to 5 substituents selected from the following substituent group B, a $C_1-C_6$ alkoxy group which is unsubstituted or substituted with 1 to 5 substituents selected from the following substituent group A, a $C_1-C_6$ alkylthio group or a phenoxy group which is unsubstituted or substituted with 1 to 5 substituents selected from the following substituent group B;

substituent group A is selected from the group consisting of a halogen atom, a $C_1-C_6$ alkoxy group, a $C_1-C_6$ alkylthio group, a cyano group and a phenyl group;

substituent group B is selected from the group consisting of a halogen atom, a $C_1-C_6$ alkyl group which is unsubstituted or substituted with 1 to 5 substituents selected from the above substituent group A, a $C_1-C_6$ alkoxy group which is unsubstituted or substituted with 1 to 5 substituents selected from the above substituent group A, a cyano group and a nitro group;

or a salt thereof.

2. The N-heteroaryl-4-(haloalkyl)nicotinamide compound or a salt thereof as claimed in claim 1, wherein R is a trifluoromethyl group.

3. The N-heteroaryl-4-(haloalkyl)nicotinamide compound or a salt thereof as claimed in claim 1, wherein $R^1$ is a hydrogen atom, a $C_1-C_4$ alkyl group which is unsubstituted or substituted (the substituent is a $C_1-C_4$ alkoxy group, a $C_1-C_4$ alkylthio group or a cyano group), a $C_3-C_4$ alkenyl group or a $C_2-C_5$ alkylcarbonyl group.

4. The N-heteroaryl-4-(haloalkyl)nicotinamide compound or a salt thereof as claimed in claim 1, wherein $R^1$ is a hydrogen atom or a $C_1-C_2$ alkyl group which is unsubstituted or substituted (the substituent is a $C_1-C_2$ alkoxy group, a $C_1-C_2$ alkylthio group or a cyano group).

5. The N-heteroaryl-4-(haloalkyl)nicotinamide compound or a salt thereof as claimed in claim 1, wherein $R^1$ is a hydrogen atom, a methyl group, a methoxymethyl group, an ethoxymethyl group or a cyanomethyl group.

6. The N-heteroaryl-4-(haloalkyl)nicotinamide compound or a salt thereof as claimed in claim 1, wherein $R^1$ is a hydrogen atom.

7. The N-heteroaryl-4-(haloalkyl)nicotinamide compound or a salt thereof as claimed in any one of claims 1 to 6, wherein $R^2$ is a hydrogen atom, a fluorine atom, a chlorine atom, a bromine atom, an iodine atom, a $C_1$–$C_4$ alkyl group which is unsubstituted or substituted with 1 to 3 substituents (the substituent or substituents being selected from the group consisting of a fluorine atom, a chlorine atom, a $C_1$–$C_4$ alkoxy group and a phenyl group), a $C_3$–$C_6$ cycloalkyl group, a $C_2$–$C_4$ alkenyl group, a $C_3$–$C_6$ cycloalkenyl group, a phenyl group which is unsubstituted or substituted with 1 to 5 substituents {the substituent or substituents being selected from the group consisting of a fluorine atom, a chlorine atom, a $C_1$–$C_4$ alkyl group which is unsubstituted or substituted with 1 to 3 substituents (the substituent or substituents being a fluorine atom or a chlorine atom), a $C_1$–$C_4$ alkoxy group which is unsubstituted or substituted with 1 to 3 substituents (the substituent or substituents being a fluorine atom or a chlorine atom), a cyano group and a nitro group}, a $C_3$–$C_4$ alkoxy group which is unsubstituted or substituted with 1 to 3 substituents (the substituent or substituents being a substituent selected from the group consisting of a fluorine atom, a chlorine atom, a $C_1$–$C_4$ alkoxy group and a phenyl group), a $C_1$–$C_4$ alkylthio group or a phenoxy group which is unsubstituted or substituted with 1 to 5 substituents {the substituent or substituents being a substituent selected from the group consisting of a fluorine atom, a chlorine atom, a $C_1$–$C_4$ alkyl group which is unsubstituted or substituted with 1 to 3 substituents (the substituent or substituents being a fluorine atom or a chlorine atom), a $C_1$–$C_4$ alkoxy group which is unsubstituted or substituted with 1 to 3 substituents (the substituent or substituents being a fluorine atom or a chlorine atom), a cyano group and a nitro group}.

8. The N-heteroaryl-4-(haloalkyl)nicotinamide compound or a salt thereof as claimed in any one of claims 1 to 6, wherein $R^2$ is a hydrogen atom, a fluorine atom, a chlorine atom, a bromine atom, an iodine atom, a $C_1$–$C_3$ alkyl group which is unsubstituted or substituted (the substituent is a $C_1$–$C_3$ alkoxy group), a $C_3$–$C_5$ cycloalkyl group, a $C_3$–$C_4$ alkenyl group, a phenyl group which is unsubstituted or substituted with 1 to 5 substituents (the substituent or substituents being selected from the group consisting of a fluorine atom, a chlorine atom, a $C_1$–$C_3$ alkyl group which is unsubstituted or substituted with a fluorine atom, a $C_1$–$C_3$ alkoxy group which is unsubstituted or substituted with a fluorine atom, a cyano group and a nitro group), a pyridyl group which is unsubstituted or substituted with 1 to 2 substituents (the substituent or substituents being selected from the group consisting of a fluorine atom, a chlorine atom and a $C_1$–$C_3$ alkyl group), a pyrazolyl group which is unsubstituted or substituted with 1 to 2 substituents (the substituent or substituents being selected from the group consisting of a fluorine atom, a chlorine atom and a $C_1$–$C_3$ alkyl group), a $C_1$–$C_3$ alkoxy group which is unsubstituted or substituted with a fluorine atom, a $C_1$–$C_3$ alkylthio group or a phenoxy group which is unsubstituted or substituted with 1 to 5 substituents (the substituent or substituents being selected from the group consisting of a fluorine atom, a chlorine atom, a $C_1$–$C_3$ alkyl group which is unsubstituted or substituted with a fluorine atom, a $C_1$–$C_3$ alkoxy group which is unsubstituted or substituted with a fluorine atom, a cyano group and a nitro group).

9. The N-heteroaryl-4-(haloalkyl)nicotinamide compound or a salt thereof as claimed in any one of claims 1 to 6, wherein $R^2$ is a hydrogen atom, a fluorine atom, a chlorine atom, a bromine atom, a $C_1$–$C_3$ alkyl group, a cyclopropyl group, an allyl group, a phenyl group, a pyridyl group, a pyrazolyl group, a $C_1$–$C_2$ alkoxy group, a $C_2$–$C_2$ alkylthio group or a phenoxy group.

10. The N-heteroaryl-4-(haloalkyl)nicotinamide compound or a salt thereof as claimed in any one of claims 1 to 6, wherein $R^2$ is a hydrogen atom, a chlorine atom, a bromine atom, a methyl group, an ethyl group or a methoxy group.

11. The N-heteroaryl-4-(haloalkyl)nicotinamide compound or a salt thereof as claimed in any one of claims 1 to 6, wherein $R^3$ is a hydrogen atom, a fluorine atom, a chlorine atom, a bromine atom, a $C_1$–$C_4$ alkyl group which is unsubstituted or substituted (the substituent is a $C_1$–$C_4$ alkoxy group), a $C_3$–$C_6$ cycloalkyl group, a formyl group, a group represented by formula CH=NOR$^{4a}$ (wherein R$^{4a}$ is a hydrogen atom or a $C_1$–$C_4$ alkyl group), a cyano group or a phenyl group which is unsubstituted or substituted {the substituent or substituents being 1 to 3 substituents, which are the same or different, selected from the group consisting of a fluorine atom, a chlorine atom, a bromine atom, a $C_1$–$C_4$ alkyl group which is unsubstituted or substituted with 1 to 3 substituents (the substituent or substituents being a fluorine atom or a chlorine atom), a $C_1$–$C_4$ alkoxy group, a cyano group and a nitro group}.

12. The N-heteroaryl-4-(haloalkyl)nicotinamide compound or a salt thereof as claimed in any one of claims 1 to 6, wherein $R^3$ is a hydrogen atom, a fluorine atom, a chlorine atom, a $C_1$–$C_2$ alkyl group which is unsubstituted or substituted (the substituent is a $C_1$–$C_2$ alkoxy group), a $C_3$–$C_5$ cycloalkyl group or a phenyl group which is unsubstituted or substituted {the substituent or substituents being 1 to 3 substituents, which are the same or different, selected from the group consisting of a fluorine atom, a chlorine atom, a $C_1$–$C_2$ alkyl group which is unsubstituted or substituted (the substituent is a fluorine atom), a $C_1$–$C_2$ alkoxy group, a cyano group and a nitro group}.

13. The N-heteroaryl-4-(haloalkyl)nicotinamide compound or a salt thereof as claimed in any one of claims 1 to 6, wherein $R^3$ is a hydrogen atom, a chlorine atom, a methyl group, a methoxymethyl group, a cyclopropyl group or a phenyl group.

14. The N-heteroaryl-4-(haloalkyl)nicotinamide compound or a salt thereof as claimed in any one of claims 1 to 6, wherein $R^3$ is a hydrogen atom or a methyl group.

15. The N-heteroaryl-4-(haloalkyl)nicotinamide compound as claimed in claim 1, which is selected from the group consisting of N-(5-isoxazolyl)-4-(trifluoromethyl)nicotinamide, N- (3-methyl-5-isoxazolyl) -4-(trifluoromethyl)nicotinamide, N- (4-chloro-5-isoxazolyl) -4-(trifluoromethyl)nicotinamide, N- (4-bromo-5-isoxazolyl) -4-(trifluoromethyl)nicotinamide, N- (4-methyl-5-isoxazolyl) -4-(trifluoromethyl)nicotinamide, N- (4-ethyl-5-isoxazolyl) -4-(trifluoromethyl)nicotinamide and N- (4-methoxy-5-isoxazolyl) -4-(trifluoromethyl)nicotinamide, or a salt thereof.

16. A pesticide composition comprising as an active component the N-heteroaryl-4-(haloalkyl)nicotinamide compound or a salt thereof claimed in any one of claims 1 to 6, and a carrier.

17. A method for producing the N-heteroaryl-4-(haloalkyl) nicotinamide compound or a salt thereof as claimed in claim 1, comprising reacting an acid halide compound represented by formula (IX):

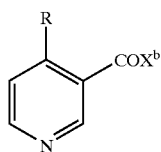

wherein R represents the same meanings as defined above, and $X^b$ represents a chlorine atom or a bromine atom, with an amino compound represented by formula (III):

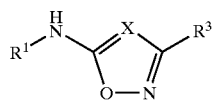

wherein $R^1$ represents a hydrogen atom, a $C_1$–$C_6$ alkyl group which is unsubstituted or substituted with 1 to 5 substituents selected from the following substituent group A, a $C_2$–$C_6$ alkenyl group or an acyl group, the acyl group is an alkylcarbonyl group which is unsubstituted or substituted with a halogen atom or a lower alkoxy group; an aliphatic acyl group which is an unsaturated alkylcarbonyl group; an arylcarbonyl group which is unsubstituted or substituted with a halogen atom, a lower alkyl group, a lower alkoxy group, a nitro group, a lower alkoxycarbonyl group or an aryl group; a lower alkoxycarbonyl group which is unsubstituted or substituted with a halogen atom or a tri-lower alkylsilyl group; an alkenyloxycarbonyl group; an aralkyloxycarbonyl group which is unsubstituted or substituted with a lower alkoxy group or a nitro group; a lower alkanesulfonyl group which is unsubstituted or substituted with a halogen atom or a lower alkoxy group; or an arylsulfonyl group which is unsubstituted or substituted with a halogen atom, a lower alkyl group, a lower alkoxy group, a nitro group, a lower alkoxycarbonyl group or an aryl group;

X represents a group represented by formula C—$R^2$;

$R^2$ and $R^3$ each independently represent a hydrogen atom, a halogen atom, a $C_1$–$C_6$ alkyl group which maybe is unsubstituted or substituted with 1 to 5 substituents selected from the following substituent group A, a $C_3$–$C_7$ cycloalkyl group, a $C_2$–$C_6$ alkenyl group, a $C_3$–$C_7$ cycloalkenyl group, a formyl group, a group represented by formula CH=$NOR^4$ (wherein $R^4$ is a hydrogen atom or a $C_1$–$C_6$ alkyl group), a cyano group, a phenyl group which is unsubstituted or substituted with 1 to 5 substituents selected from the following substituent group B, a $C_1$–$C_6$ alkoxy group which is unsubstituted or substituted with 1 to 5 substituents selected from the following substituent group A, a $C_1$–$C_6$ alkylthio group or a phenoxy group which is unsubstituted or substituted with 1 to 5 substituents selected from the following substituent group B;

substituent group A is selected from the group consisting of a halogen atom, a $C_1$–$C_6$ alkoxy group, a $C_1$–$C_6$ alkylthio group, a cyano group and a phenyl group;

substituent group B is selected from the group consisting of a halogen atom, a $C_1$–$C_6$ alkyl group which maybe is unsubstituted or substituted with 1 to 5 substituents selected from the above substituent group A, a $C_1$–$C_6$ alkoxy group which is unsubstituted or substituted with 1 to 5 substituents selected from the above substituent group A, a cyano group and a nitro group, optionally followed by an alkylation, an alkenylation or an acylation, to produce an N-heteroaryl-4-(haloalkyl) nicotinamide compound represented by formula (I):

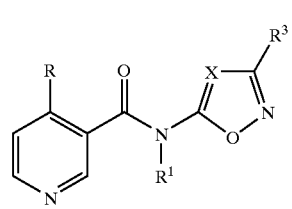

wherein R, X, $R^1$ and $R^3$ represent the same meanings as defined above, or a salt thereof.

18. The N-heteroaryl-4-(haloalkyl) nicotinamide compound or a salt thereof as claimed in claim 1, wherein the compound is N- (4-methyl-5-isoxazolyl) -4-(trifluoromethyl) nicotinamide.

19. The N-heteroaryl-4-(haloalkyl) nicotinamide compound or a salt thereof as claimed in claim 1, wherein the acyl group is a $C_2$–$C_5$ alkylcarbonyl group.

20. The N-heteroaryl-4-(haloalkyl) nicotinamide compound or a salt thereof as claimed in claim 1, wherein the acyl group is an acetyl group.

* * * * *